(12) United States Patent
Riggs et al.

(10) Patent No.: US 6,593,120 B1
(45) Date of Patent: Jul. 15, 2003

(54) RECOMBINANT DNA ENCODING A REVERSE TRANSCRIPTASE DERIVED FROM MOLONEY MURINE LEUKEMIA VIRUS

(75) Inventors: Michael G. Riggs, San Diego, CA (US); Matthew Sorensen, Irvine, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 09/397,955

(22) Filed: Sep. 15, 1999

Related U.S. Application Data

(63) Continuation-in-part of application No. 08/821,948, filed on Mar. 21, 1997, now Pat. No. 5,998,195, which is a continuation of application No. 08/443,781, filed on May 18, 1995, now abandoned, which is a continuation of application No. 08/221,804, filed on Apr. 1, 1994, now abandoned.

(51) Int. Cl.[7] .......................... C12N 9/12; C12N 15/70; C12N 1/20; C12P 21/06; C07H 21/04
(52) U.S. Cl. ............... 435/194; 435/320.1; 435/252.33; 435/252.3; 435/69.1; 435/325; 536/23.1; 536/23.2
(58) Field of Search ............................. 435/194, 320.1, 435/325, 69.1, 252.3, 252.33; 536/23.2, 23.1

(56) References Cited

U.S. PATENT DOCUMENTS

| | | | |
|---|---|---|---|
| 4,663,290 A | 5/1987 | Weis et al. | 435/253 |
| 4,943,531 A | 7/1990 | Goff et al. | 435/194 |
| 5,017,492 A | 5/1991 | Kotewicz et al. | 435/68 |
| 5,017,493 A * | 5/1991 | Andersen et al. | 435/252.3 |
| 5,244,797 A | 9/1993 | Kotewicz et al. | 435/194 |
| 5,405,776 A | 4/1995 | Kotewicz et al. | 435/252.33 |
| 5,668,005 A | 9/1997 | Kotewicz et al. | 435/194 |
| 5,804,421 A | 9/1998 | Vinik et al. | 435/69.1 |

FOREIGN PATENT DOCUMENTS

| | | |
|---|---|---|
| WO | 9807869 | 2/1998 |
| WO | 9844161 | 10/1998 |

OTHER PUBLICATIONS

Le Grice, S. et al., Eur. J. Biochem., vol. 187, pp. 307–314, 1990.*
Amann et al., "Tightly regulated tac promoter vectors useful for the expression of unfused and fused proteins in *Escherichia coli*", *Gene*, 69:301–315 (1988).
Durwald et al., "Endonuclease I–deficient and ribonuclease I–deficient *Escherichia coli* mutants", *J. Mol. Biol.*, 34:331–346 (1968).
Gu et al. "Recombinant Proteins Attached to a Nickel–NTA Column: Use in Affinity Purification of Antibodies," *BioTechniques*, 17(2):257–262 (1994).
Hautala et al., "Increased expression of a euraryotic gene in *Escherichia coli* through stabilization of its messenger RNA", *Proc. Natl. Acad. Sci. USA*, 76(11):5774–5778 (1979).
Hizi et al., "Expression in *Escherichia coli* of a Moloney murine Leukemia virus reverse transcriptase whose structure closely resembles the viral enzyme", *Gene*, 66:319–323 (1988).
Hu et al., Murine leukemia virus pol gene products: analysis with antisera generated against reverse transcriptase and endonuclease fusion proteins expressed in *Escherichia coli*, *J. Virol.*, 60(1):267–271 (1986).
Kelly et al. "RNase PH is Essential for tRNA Processing and Viability in RNase–deficient *Escherichia coli* Cells", *J. Biol. Chem.*, 267(23):16015–16018 (1992).
Kotewicz et al., "Cloning and overexpression of Moloney murine leukemia virus reverse transcriptase in *Escherichia coli*", *Gene*, 35:249–258 (1985).
Petty, K.J., "Metal–Chelate Affinity Chromatography", In Ausubel F.M. et al., eds., Current Protocols in *Molecular Biology*, vol. 2, pp. 10.11.10–10.11.24 (1996) (John Wiley & Sons, New York, NY).
Sisk et al., "High–Level Expression and Purification of Secreted Forms of Herpes Simplex Virus Type 1 Glycoprotein gD Synthesized by Baculovirus–Infection Insect Cells", *J. Virol.*, 68(2):766–775 (1994).
Telesnitsky et al., "RNase H domain mutations affect the interaction between Moloney murine leukemia virus reverse transcriptase and its primer template", *Proc. Natl. Acad. Sci. USA*, 90:1276–1280 (1993).

* cited by examiner

*Primary Examiner*—Rebecca E. Prouty
*Assistant Examiner*—Delia Ramirez
(74) *Attorney, Agent, or Firm*—Christine A. Gritzmacher; Carlos A. Fisher

(57) ABSTRACT

A recombinant plasmid for expression of Moloney Murine Leukemia Virus (MMLV)-derived reverse transcriptase in *E. coli* cells deficient in the expression of RNAse activity, a method for purification of the recombinant enzyme, and a purified recombinant reverse transcriptase for suitable use in cDNA and nucleic acid amplification procedures are disclosed.

10 Claims, 14 Drawing Sheets pUC 18  AGGAAACAGCTATG.ACC.ATG.ATT.ACG.AAT.TC pUC 18N  AGGAAACAGCCATG.GCC.ATG.ATT.ACG.AAT.TC
                     Nco I                         Eco R I
ribosome
binding
site

|          |     | Pvu II site |
|----------|-----|-------------|
| Oligo #1 | 5'- | GGCATGCAGCTGGCCACGACAGGTTCCCGACTGGAAA |
| Oligo #1 |     | GCGGGCAGTGAGCGCAACGCAATTAATGTGAGTAGCT |
| Oligo #1 |     | CACTCATTAGGCACCCCAGGCTTTACACTTTATGCTTCC -3' |
| Oligo #2 | 3'- | CCGTGGGGTCCGAAATGTGAAATACGAAGG |
| Oligo #2 |     | CCGAGCATACAACACACCTAACACTCGCCTATTTGAAA |
| Oligo #2 |     | GTGTGTCCTTTGTCGGTACCGGTACTAATGCTTAAGCTCGAA -5' |
|          |     | Eco RI site |

FIG. 2

| | | Distance from RBS to ATG |
|---|---|---|
| E. coli 16S rRNA 3'-5' | (3' end) ATT CCTCCACTAGGT T...... | |
| pUC lacZ | CACACAGGAAACAGCT ATG | 7 |
| pUC18N lacZ | CACACAGGAAACAGCC ATG G | 7 |
| Jespers et al "R" gene (natural) | AAAGCCCGGAGTAGAAG ATG | 6 |
| Jespers et al "R" gene (improved) | ATATAAGGAGGTTTAAAAT ATG | 7 |
| Jay et al synthetic (improved) | GCATAAGGAGGTTTAAGCT (4-5 bases) | (11-12) |
| SD7 | CACTAAGGAGGTTTAAACC ATG G | 7 |
| SD8 | CACTAAGGAGGTTTAAg/t ACC ATG G | 8 |
| SD9 | CACTAAGGAGGTTTAAg/tg/t ACC ATG G | 9 |

FIG. 3

| | 5'- | | |
|---|---|---|---|
| Oligo #5 | GAGCTCGAATTCGTAATCATGGCCATGG | | TTAAACCTCCTTAGTG |
| Oligo #6 | GAGCTCGAATTCGTAATCATGGCCATGGT at | | TTAAACCTCCTTAGTG |
| Oligo #7 | GAGCTCGAATTCGTAATCATGGCCATGGT at at | | TTAAACCTCCTTAGTG |

| | |
|---|---|
| Oligo #5 | AAATTGTTATCCGCTCACAATTCCACACAACATACGAGCCGGAAGCAT |
| Oligo #6 | AAATTGTTATCCGCTCACAATTCCACACAACATACGAGCCGGAAGCAT |
| Oligo #7 | AAATTGTTATCCGCTCACAATTCCACACAACATACGAGCCGGAAGCAT |

| | |
|---|---|
| Oligo #5 | AAAGTGTAAAGCCTGGGGTGCC -3' |
| Oligo #6 | AAAGTGTAAAGCCTGGGGTGCC |
| Oligo #7 | AAAGTGTAAAGCCTGGGGTGCC |

FIG. 4

Oligomer #8  5'-      AGGCAGCCATCACAGAGACTCCAGACACCTCTACCCTCCTCTAATA     -3'
Oligomer #9  3'-CTTTCCGTCGGTAGTGTCTCTGAGGTCTGTGGAGATGGGAGGAGATTATTCGA-5'

FIG. 7

SEQ ID NO:

14
5' GCTGCTCCATG GGT CAC CAT CAC CAT CAC CAT CTG AAC ATC GAA GAT GAG CAT CGG C 3'
Spacer  NcoI        6x His                                                
         Start Gly 15
3' CAACCTGGTCCCTTATGACCATGGTGCTGC 5'
              KpnI  Spacer 16
5' CATCATAGATCTTGGCCCCTACTAAAGCCC 3'
   Spacer  BglII 17
3' CTC TGA GGT CTG TGG AGA TGG GAG GAG GAG GTA GTG GTA GTG GTA GTG ATT CGAA AACAAC 5'
       Stop           6x His                                          Hind III  Spacer

FIG. 12

RECOMBINANT DNA ENCODING A REVERSE TRANSCRIPTASE DERIVED FROM MOLONEY MURINE LEUKEMIA VIRUS

CROSS-REFERENCE TO RELATED APPLICATIONS

This application is a continuation in part of pending Ser. No. 08/821,948, filed Mar. 21, 1997, now U.S. Pat. No. 5,998,195 which is a continuation of Ser. No. 08/443,781, filed May 18, 1995, now abandoned, which is a continuation of Ser. No. 08/221,804, filed Apr. 1, 1994, now abandoned, to which priority is claimed all of which are incorporated herein by reference.

FIELD OF THE INVENTION

The invention relates to recombinant proteins, particularly to viral reverse transcriptase enzymes produced by recombinant DNA technology, and specifically relates to reverse transcriptase derived from Moloney Murine Leukemia virus (MMLV) that is expressed from recombinant DNA in a bacterial host cell and that includes multiple histidine residues.

BACKGROUND OF THE INVENTION

Retroviruses are a group of viruses whose genetic material consists of single-stranded RNA. Following adsorption and entry of retroviral RNA into the host cell, the viral RNA is used as a template for synthesis of a complementary DNA (cDNA) strand. The cDNA is then made double-stranded through the action of an enzyme having DNA polymerase activity; this double-stranded DNA integrates into the host genome. The RNA-directed DNA polymerase activity responsible for the synthesis of cDNA from the viral RNA template is commonly called reverse transcriptase ("RT").

A number of retroviruses have been implicated as the causative agents of various cancers, and other diseases. A retrovirus, human immunodeficiency virus-1 (HIV-1), is the causal agent of acquired immunodeficiency syndrome (AIDS). Also, reverse transcriptase enzymes have become important reagents in molecular biology because of their ability to make cDNA from almost any RNA template. Reverse transcriptase is commonly used to make nucleic acids for hybridization probes and to convert single-stranded RNA into a double-stranded DNA for subsequent cloning and expression.

Reverse transcriptases have been used as a component of transcription-based amplification systems. These systems amplify RNA and DNA target sequences up to 1-trillion fold and have been previously described in detail (see Burg et al., PCT Patent Application WO 89/01050 (1988) and U.S. Pat. No. 5,437,990; Gingeras et al., PCT Patent Application WO 88/10315 (1988); Gingeras et al., European Patent Application EPO 0373960 (1989); Davey & Malek, European Patent Application EPO 0329822 (1988); Malek & Davey, PCT Patent Application WO 91/02814 (1989); Davey et al., U.S. Pat. Nos. 5,409,818 and 5,554,517; Davey et al., U.S. Pat. No. 5,466,586; Malek et al., U.S. Pat. No. 5,130,238; Kacian et al., European Patent Application EPO 0408295 A2 (1990) and U.S. Pat. Nos. 5, 399,491, 5,480,784, 5,824,518, 5,888,779 and 5,554,516), the experimental details of which are hereby incorporated by reference herein.

Some transcription-based amplification methods are especially convenient because the amplification reactions are isothermal. These systems are particularly suited for diagnostic tests in clinical laboratories. For example, detection of pathogens causing infectious diseases and gene sequences associated with cancers or genetic diseases are important uses of such tests. Reverse transcriptases are also employed as an initial step in some protocols in which the polymerase chain reaction (PCR) amplifies an RNA target (see Malek et al., U.S. Pat. No. 5,130,238 (1992); and Mocharla et al., 1990, *Gene* 99:271–275). In RT-PCR procedures, the reverse transcriptase is used to make an initial cDNA copy of the RNA target, which is then amplified by successive rounds of DNA replication using PCR.

Retroviral reverse transcriptases have three enzymatic activities: RNA-directed DNA polymerase activity, DNA-directed DNA polymerase activity, and RNAse H activity (Verma I., 1977, *Biochim. Biophys. Acta* 473: 1–38). The latter activity specifically degrades RNA contained in an RNA:DNA duplex. RNA strand degradation in RNA:DNA intermediates by RNAse H is an important component of some transcription-based amplification systems. RNAse H-mediated degradation of RNA is distinguishable from unwanted degradation due to contaminating nucleases, which interferes with amplification.

A disadvantage of the transcription-based amplification systems is their sensitivity to even trace amounts of nucleases. Because a number of important diseases may yield samples containing very few target nucleic acid molecules, detection of small amounts of target is often crucial for an accurate and timely diagnosis. Indeed, target amplification methods are most valuable when the number of target molecules is low. With low levels of input target nucleic acids, unwanted degradation of RNA targets, or of RNA or DNA reaction intermediates, can lead to amplification failures and consequent inaccurate diagnosis. Ribonuclease contamination is also a problem in RT-PCR reactions, because RNA target loss can result in amplification failure.

Ribonucleases are relatively ubiquitous and occur in high concentrations in a variety of biological materials, including in retrovirus preparations and cells commonly used to express recombinant proteins. Ribonucleases ("RNases") frequently contaminate RT preparations from a variety of sources and can interfere with cDNA synthesis, probe preparation and other uses besides target amplification. Often, an RNase inhibitor is added to a reaction mixture to minimize the deleterious effects of this contamination (e.g., see Sambrook et al., 1989, *Molecular Cloning: A Laboratory Manual* (2d ed., Cold Spring Harbor Laboratory Press, Cold Spring Harbor, N.Y.), pp. 8.11–8.13).

Commonly-used substances that inhibit or inactivate RNases, including detergents, chaotropes, organics, metals, proteases and metals are inappropriate for use in target amplification systems because they also inhibit the enzymes used for amplification. RNase-inhibiting proteins, e.g. human placental RNase inhibitor (Blackburn et al., 1977, *J. Biol. Chem.* 252: 5904) or rat liver RNase inhibitor (Gribnau et al., 1969, *Arch. Biochem. Biophys.* 130: 48–52), may be unstable, are expensive, and can contribute additional interfering substances, such as nucleic acids and RNases that are not inhibited by the inhibitor.

In addition to nucleases, traces of other enzymes, nucleic acids, and certain buffer salts may interfere with amplification reactions. While these substances are merely undesirable for many uses of RT, because of the nature of the amplification reaction, it is critical that RT preparation contain as little contaminating substances as possible.

Reverse transcriptases have been isolated and purified from various sources. When RT is isolated directly from virus particles, cells or tissues, high costs may preclude their widespread use in diagnostic tests (e.g., see Kacian et al., 1971, *Biochim. Biophys. Acta* 46: 365–83; Yang et al., 1972, *Biochem. Biophys. Res. Comm.* 47: 505–11; Gerard, et al., 1975, *J. Virol.* 15: 785–97; Liu et al., 1977, *Arch. Virol.* 55 187–200; Kato et al., 1984, *J. Virol. Methods* 9: 325–39; Luke et al., 1990, *Biochem.* 29: 1764–69 and Le Grice et al., 1991, *J. Virol.* 65: 7004–07). Also, these methods have not assured removal of inhibitors or contaminants that interfere with target amplification reactions. Another important consideration for a variety of reverse transcriptase uses is the RT-associated RNase H activity. The amount of RNase H activity and coordination of RNase H activity with the RNA- and DNA-dependent RT activities are important features that affect an enzyme's utility for various purposes, including transcription-based amplification systems. Too much or too little activity, inappropriate activity (e.g., non-specific RNase activity), or poorly-coordinated RNase H and DNA synthesis activities can all lead to reduced performance. Proper balance of the synthetic and degradative activities must be maintained; this is not only a function of the particular RT used, but also depends on the ability of a purification protocol to remove inappropriate RNase and/or DNase activities.

Reverse transcriptase genes have been cloned and expressed in bacterial hosts. Attempts to clone and express in *E. coli* a gene encoding reverse transcriptase from avian myeloblastosis virus (AMV-RT) did not lead to production of significant amounts of purified enzyme. This is probably because AMV-RT consists of two polypeptide chains (α and β) which must form a dimer and undergo specific post-translational modifications to produce a fully active enzyme. These modifications do not occur in *E. coli*.

In contrast to AMV-RT, many reverse transcriptases derived from mammalian viruses consist of only one polypeptide chain; cloning and expression of these enzymes have been more successful. Goff et al. (U.S. Pat. No. 4,943,531) and Kotewicz et al. (U.S. Pat. No. 5,017,492) have described methods for the purification of reverse transcriptase derived from Moloney Murine Leukemia Virus (MMLV-RT) and expressed in *E. coli*. These methods form the basis of many commercially available RT.

Some protein purification methods use affinity tags attached to the protein of interest which is used to select the protein of interest from a mixture by binding the affinity tag to its ligand. Affinity tags include, for example, histidine residues, glutathione S-transferase, Protein A or maltose binding protein.

Many commercial RT preparations have been found unsuitable for use in target amplification and for other purposes due to nuclease contamination (Sambrook et al., 1989, *Molecular Cloning: A Laboratory Manual* (2d ed., Cold Spring Harbor Laboratory Press, Cold Spring Harbor, N.Y.); Ryskov et al.,1982, *Mol. Biol. Rep.* 8: 213–16). Other problems with commercial MMLV-RT preparations may be related to an altered coordination between the DNA synthesis and RNAse H activities of the purified enzyme, reduced ability to bind and initiate synthesis at primer sites or to read through regions of tight secondary structure, or contaminating DNase and other proteins (Agronovsky A. A., 1992, *Anal. Biochem.* 203: 163–65). Also, commercial preparations made using the previously available purification methods show significant lot-to-lot variability. Moreover, due in part to lengthy and labor-intensive purification procedures, the expense of the reagents and scale-up equipment, and the low enzyme yields, the cost is prohibitive for widespread commercial application of the enzymes in target amplification systems.

It is therefore an object of the present invention to provide an improved form of reverse transcriptase having the correct balance of DNA synthetic activities and RNAse H digestive activities, thereby being particularly suited for use in nucleic acid amplification methods.

It is another object of the present invention to provide a convenient source of reverse transcriptase containing low levels of contaminants (e.g., undesired RNases) that interfere with transcription-based amplification reactions by cloning and expressing a gene encoding MMLV-RT having these properties in an *E. coli* host.

It is another object of the present invention to reduce the RNase activity associated with the enzyme prior to and following purification by cloning and expressing the MMLV-RT gene in a ribonuclease-deficient strain of *E. coli*.

It is another object of the present invention to develop a simple purification scheme for the isolation of the RT enzyme.

It is also an object of the present invention to provide methods for the purification of the enzyme that achieve high levels of RT purity at a low cost.

SUMMARY OF THE INVENTION

The present invention features an expression vector or plasmid containing a cloned version of the gene for MMLV-RT which, when used to transform a suitable host cell such as *E. coli*, leads to expression of the gene and generation of a gene product having the DNA- and RNA-directed DNA polymerase activities and RNAse H activity associated with retroviral reverse transcriptases.

The present invention also features a plasmid containing a MMLV-RT gene inserted into a host cell which has a reduced level of ribonuclease activity as compared to wild-type strains.

The present invention also includes methods for the purification of the resulting enzyme from the host cells, such methods comprising suitable growth media, fermentation conditions, harvesting and storage of the cells, cell lysis and chromatography.

The present invention also features the enzyme produced by the expression vectors, host cells, and purification procedures of the present invention. The enzyme is highly-purified and suitable for use in nucleic acid amplification and other genetic engineering procedures.

The present invention features the use of the enzyme produced by the methods described herein for the synthesis of cDNA for a variety of purposes, notably in transcription-based amplification and RT-PCR reactions.

According to one aspect of the invention, there is provided a recombinant DNA molecule that includes a DNA fragment containing a DNA sequence encoding a single-chain polypeptide derived from Moloney murine leukemia virus (MMLV) having RNA-directed and DNA-directed DNA polymerase activities and RNase H activity and encoding a plurality of contiguous histidine residues in then single-chain polypeptide; a DNA fragment comprising a promoter sequence for expressing the gene encoding the single-chain polypeptide in an *E. coli* host cell; and a DNA fragment containing an origin of replication that promotes autonomous replication of a vector in an *E. coli* host cell. In the recombinant DNA molecule, the DNA fragments are operably linked so that the fragments are replicated together in the *E. coli* host cell and the DNA sequence encoding the single-chain polypeptide is expressed in the *E. coli* host cell to produce the single chain polypeptide. In one embodiment, the DNA sequence encoding the plurality of contiguous histidine residues is located at or near the 5' or 3' end of the DNA sequence encoding the single-chain polypeptide derived from MMLV. In another embodiment, the DNA sequence encoding the plurality of contiguous histidine residues encodes six histidine residues. The DNA sequence encoding the plurality of contiguous histidine residues may be located adjacent to a codon encoding an amino terminal glycine residue of the single-chain polypeptide derived from MMLV, or may be located adjacent to a codon encoding a carboxyl-terminal stop signal for expression of the single-chain polypeptide derived from MMLV in the *E. coli* host cell.

According to another aspect of the invention, there is provided a method for producing a polypeptide having RNA-directed and DNA-directed DNA polymerase activities. The method includes the steps of providing a plasmid comprising a DNA sequence derived from a Moloney murine leukemia virus (MMLV) sequence and encoding a single-chain polypeptide having RNA-directed and DNA-directed DNA polymerase activities and RNase H activity, codons encoding a plurality of contiguous histidine residues located at or near either an amino-terminus or carboxyl-terminus of the single-chain polypeptide, at least one selectable marker gene, a promoter sequence for expression of the DNA sequence derived from MMLV in an *E. coli* host cell, and an origin of replication for autonomous replication of the plasmid within an *E. coli* host cell and growing *E. coli* host cells containing the plasmid in a liquid culture that promotes cell division and expression of the DNA sequence derived from MMLV. Then, the method includes lysing the *E. coli* host cells to form a cell lysate; and purifying the single-chain polypeptide from the cell lysate using metal ion affinity chromatography that uses the contiguous histidine residues present in the single-chain polypeptide. In one embodiment, the metal ion affinity chromatography is performed using nickel ions attached to a resin to retain a His-tagged reverse transcriptase enzyme derived from the MMLV sequence. In another embodiment, the His-tagged reverse transcriptase enzyme is eluted from the nickel ions attached to the resin using an imidazole-containing buffer. The single-chain polypeptide purified using metal ion affinity chromatography preferably has an apparent molecular weight of about 70,000 daltons. The single-chain polypeptide purified using metal ion affinity chromatography preferably has DNA-directed DNA polymerase activity having a specific activity of at least about 275 U/mg as determined using a primer extension reaction and by comparison to DNA-directed DNA polymerase activity of a known reverse transcriptase enzyme.

BRIEF DESCRIPTION OF THE DRAWINGS

FIG. 2 shows the sequences of oligonucleotides (Oligo #1 and Oligo #2, SEQ ID NO:1 and SEQ ID NO:2, respectively) used to construct plasmid pUC 18N.

FIG. 3 shows alignments of sequences of *E. coli* 16S rRNA and of the ribosome binding sites ("RBS") of sequences from pUC lacZ , pUC 18N lacZ , the natural "R" gene of Jespers et al. (1991, *Protein Engineering* 4: 485–92), the improved "R" gene of Jespers et al., the synthetic improved sequence of Jay et al. (1981, *Proc. Natl. Acad. Sci. USA* 78: 5543–48) and the present constructs SD7, SD8 and SD9, with the distances from the RBS to the initiating "ATG" codon shown at the right of each sequence.

FIG. 4 shows the sequences of three oligonucleotides used to modify the ribosome binding site and spacer region of improved RBS vectors of the present invention: Oligo #5 (SEQ ID NO:5), Oligo #6 (SEQ ID NO:6) and Oligo #7 (SEQ ID NO:7), where "at" in a box indicates either A or T at that position.

FIG. 7 shows the aligned sequences of Oligomer #8 (SEQ ID NO:10), in 5'-3' orientation, and Oligomer #9 (SEQ ID NO:11), in 3'-5' orientation, that were used to construct pUC18 MMLV Tailed.

FIG. 8A shows, between the arrows pointing to the Mam I to Hind III restriction endonuclease sites, the 1997 bp RT fragment shown as fragment (3) derived from pUC18 MMLV III Tailed; FIG. 8B shows fragment (2) which is formed of synthetic oligomers, having an Nco I sequence at one end and a Mam I sequence at the other end; FIG. 8C shows fragment (1) between the arrows extending from a Hind III site to an Nco I site, derived from the pUC18N vector; FIG. 8D shows plasmid pUC 18N MMLV Gly made up of linked fragments (1), (2) and (3), as in FIGS. 8A-8C; FIG. 8E shows the Aat II fragment containing a tetracycline-resistance gene ("Tet") derived from pUC Tet(+); and FIG. 8F shows the orientation of the Tet gene relative to the glycine-encoding first codon ("Gly first codon") in the plasmid pUC 18N MMLV Gly Tet(−).

FIG. 9A shows pUC18N MMLV Gly Tet(−) containing fragment (2) indicated by the arrows extending from the Nco I site near the Gly first codon to a Hind III site; FIG. 9B shows pUC18N SD9D containing fragment (1) indicated by the arrows extending from the Nco I site and a Hind III site which contains an improved ribosome binding site, vector sequence and an Amp gene; FIG. 9C shows plasmid pUC18N SD9D MMLV Gly made up of fragments (1) and (2), as in FIGS. 9A and 9B, linked at the Nco I and Hind III sites; FIG. 9D shows the Aat II fragment containing a Tet gene in pUC Tet(+), as in FIG. 8E; and FIG. 9E shows the orientation of the Tet gene relative to the improved ribosome binding site and Gly first codon in the plasmid pUC 18N SD9D MMLV Gly Tet(−).

FIG. 12 shows the sequences of primers having SEQ ID NO:14 (5' to 3'), SEQ ID NO:15 (3' to 5'), SEQ ID NO:16 (5' to 3') and SEQ ID NO:17 (3' to 5') with terminal "spacer" sequences, restriction endonuclease recognition sequences (Nco I, Kpn I, Bgl II, Hind III), histidine encoding codons ("6xHis") and "Start", "Stop" and glycine encoding ("Gly") codons marked by lines above and below the sequence.

DETAILED DESCRIPTION OF THE INVENTION

Definitions

Figures 1A, 1B:
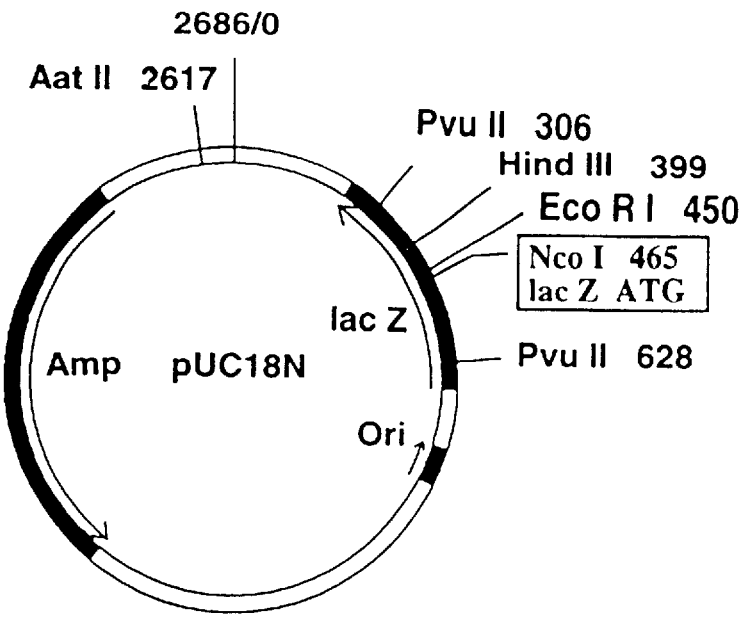
FIG. 1A shows a schematic diagram of plasmid pUC18N, with locations of restriction endonuclease recognition sites shown outside of the circle and locations of the lacZ and ampicillin-resistance ("Amp") genes and the origin of replication ("Ori") shown inside of the circle.
FIG. 1B shows sequences near the ribosome binding site of plasmid pUC 18 (upper line) that were changed in construction of plasmid pUC 18N (lower line), forming an Nco I endonuclease recognition sequence.

As used herein the following terms have the indicated meanings unless expressly indicated otherwise. Undefined terms are given their usually accepted meaning in the art.

By "selectable marker gene" is meant a DNA fragment encoding a gene that, when carried and expressed by a host cell, confers a growth advantage to the host cell, compared to cells not containing the selectable marker gene, when both are grown in a culture media of a given composition. For example, the β-lactamase gene confers resistance to ampicillin on host cells containing this gene, whereas cells not containing the β-lactamase gene are sensitive to ampicillin; thus, only cells expressing the β-lactamase gene grow in ampicillin-containing media. Similarly, cells unable to catabolize an essential amino acid do not grow in a medium that does not contain that amino acid, whereas cells containing a gene that allows the cell to make the essential amino acid grow in the same medium. A selectable marker gene may be covalently linked, e.g. in a plasmid or expression vector, to one or more other "silent" genes or genetic elements to allow identification of cells containing both the selectable gene and the silent gene(s) and/or genetic element (s).

By "purified" nucleic acid or protein is meant a nucleic acid or protein subjected to at least one step that removes cellular components such as carbohydrates, lipids, unwanted nucleic acids, or unwanted proteins from the indicated nucleic acid or protein.

By "upstream" is meant to the 5' side of a given locus on a nucleic acid strand, or to the 5' side of a locus with respect to the direction of gene transcription in that region of a double-stranded nucleic acid.

By "downstream" is meant to the 3' side of a given locus on a nucleic acid strand, or to the 3' side of a locus with respect to the direction of gene transcription in that region of a double-stranded nucleic acid.

By "$T_m$" is meant the temperature at which 50% of a population of a double-stranded nucleic acid molecules, or nucleic acid molecules having a double-stranded region, become single-stranded or thermally denatured.

By "recombinant" is meant a nucleic acid molecule or protein that, at least partially, results from use of in vitro biochemical techniques.

A "recombinant DNA molecule" is a non-naturally occurring DNA molecule that may include, but is not limited to, molecules that comprise restriction endonuclease fragments, in vitro nucleic acid ligation products, in vitro exonuclease fragments, and expression vectors comprising heterologous genetic elements such as one or more of the following: promoters, repressor genes, selectable marker genes, temperature-sensitive DNA replication elements, structural genes, and the like.

A "recombinant protein" or enzyme is one that is not found in nature and may include, but is not limited to, purified protein preparations and proteins produced by expression of recombinant DNA molecules. The latter proteins are usually expressed in a heterologous host cell, i.e., one in which the native protein or enzyme is not produced. The gene encoding a recombinant protein may reside on an expression vector contained within a host cell of the same species as the organism from which the protein was derived.

By "truncated" is meant a smaller version of a gene or protein. With respect to the primary nucleotide or amino acid sequence, a truncated form of a reference nucleic acid or protein is one that lacks one or more nucleotides or amino acids as compared to the reference nucleic acid or protein.

By "substantial sequence homology" is meant that a first nucleic acid or protein molecule has a recognizably nonrandom similarity to a second reference nucleic acid or protein over at least about 89% of its nucleotide or amino acid sequence, respectively.

By a nucleic acid or protein "domain" is meant at least one definite region of contiguous nucleotide or amino acid residues.

By "origin of replication" is meant a specific region of DNA at which primer production and initiation of DNA polymerase activity begins. Herein, the term is used to mean a nucleic acid element in a DNA expression vector that allows the expression vector to increase in copy number within a given host cell.

By "promoter" is meant a genetic element comprising a specific region of DNA at which an RNA polymerase enzyme can bind and begin transcription of a DNA template, thus providing the first step of translating the genetic information contained in a nucleic acid sequence to produce a protein of an amino acid sequence corresponding to the nucleic acid sequence.

By "expression", "gene expression" or "protein expression" is meant the production of protein from information contained within a gene by a host organism.

By "transformation" is meant a biochemical method of inducing a host cell to internalize a nucleic acid molecule. Such nucleic acid molecules are usually genetic elements comprising at least an origin of replication, a selectable marker gene, and a promoter for expression of the selectable marker gene within the host cell.

By "heterologous" is meant not of the same species. Thus, an enzyme expressed in a heterologous host cell is produced in a host cell of a different species than the one from which the enzyme was originally derived.

By "gene" is meant a nucleic acid region having a nucleotide sequence that encodes an expressible protein or polypeptide. A gene may comprise one or more "coding sequences" containing codons that encode amino acid residues of the expressed protein; the gene may also, but need not, comprise one or more "non-coding" nucleotide sequence regions that do not contain codons encoding amino acid residues of the expressed protein.

By "His tag" is meant an amino acid sequence of three or more, preferably six, contiguous histidine residues that are covalently added to a protein of interest, usually by construction and expression of a recombinant gene encoding the histidine residues adjacent to or within the amino acid sequence of the protein of interest. A protein containing a His tag may be referred to as a "His-tagged" protein. DNA encoding the histidine residues may be referred to as "His-tag codons".

All of the biochemical techniques used for construction and evaluation of the MMLV-RT expression vectors including, but not limited to, restriction digestion protocols, gel electrophoresis, Southern blot, and DNA modification reactions, are known to those of ordinary skill in the art (e.g., see Sambrook et al., 1989, *Molecular Cloning: A Laboratory Manual* (2d ed., Cold Spring Harbor Laboratory Press, Cold Spring Harbor, N.Y.)) and have been previously described in detail (PCT Patent Application WO 9527067).

I. Construction of the Cloning Vector a. Plasmid pUC18N (FIG. 1A)

Plasmid pUC18 (Life Technologies, Inc., Bethesda, Md.) was used as the parent vector. Clones were screened by well-known restriction mapping techniques using agarose gels. An Nco I restriction site was introduced between the lac Z ribosome binding site and the Eco RI restriction site of pUC18 by making a substitution of two nucleotide bases, as shown in FIG. 1B. The mutations were introduced using the two synthetic oligonucleotides shown in FIG. 2 as Oligo #1 and Oligo #2 (SEQ ID NOS:1 and 2, respectively). As shown in FIG. 2, the oligonucleotides overlap by 30 complementary bases at their 3' ends. The oligonucleotides were allowed to hybridize, filled in using the Klenow fragment of *E. coli* DNA polymerase I, and digested with Pvu II and Eco RI. Plasmid pUC18 was digested with Eco RI and partially digested with Pvu II to yield two DNA fragments: a larger fragment including the intact ampicillin resistance gene (Amp), the origin of replication (Ori), and part of the lac Z gene. The smaller Eco RI-Pvu II fragment consisted of the portion of the lac Z gene corresponding to positions 450 to 628 of the pUC18 map. The synthetic Eco RI-Pvu II fragment was inserted into the larger vector fragment, ligated and used to transform *E. coli* strain JM 109. Clones containing properly constructed vectors produced a blue color using an X-gal (5-bromo-4-chloro-3-indolyl-β-D-galactoside) substrate, indicating that the lac Z gene had been properly reconstructed. These results were further verified by restriction mapping. This vector was named pUC18N (FIG. 1A).

b. Construction of Plasmids Containing the Reverse Transcriptase Gene

Figure 5:
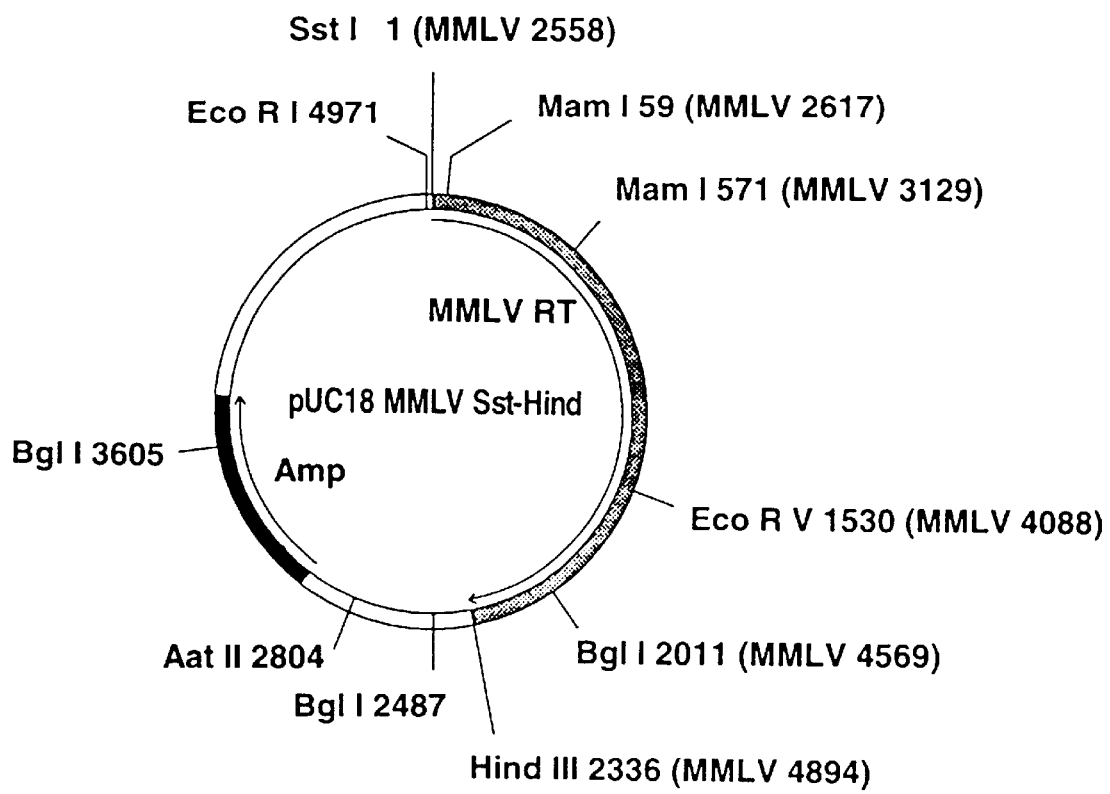
FIG. 5 shows a schematic diagram of the sequences used to construct plasmid "pUC18 MMLV Sst-Hind", where RT sequences derived from Moloney Murine Leukemia virus ("MMLV RT") are shown in gray, sequences derived from the vector are shown in white and the gene for ampicilin resistance ("Amp") is shown in solid, with locations of restriction endonuclease recognition sequences (Eco RI, Sst I, Mam I, Eco RV, Bgl I, Hind III and Aat II) indicated outside of the circle with the corresponding MMLV locations shown in parentheses.

The intact MMLV gene was isolated as an Sst I-Hind III fragment from the pMMLV-L clone as described by Miller and Verma (1984, *J. Virol.* 49:214–222). This fragment contained the nucleotide sequence corresponding to the region from MMLV position 2558 (Sst I site) to position 4894 (Hind III site) and contained the entire RT gene between 40 extra upstream bases and 284 extra downstream bases. Plasmid vector pUC18 was digested with Sst I and Hind III, and the vector and RT gene were ligated together and used to transform competent *E. coli* DH5αf cells (Life Technologies, Gaithersburg, Md.). The resulting plasmid was named pUC18 MMLV Sst-Hind (FIG. 5).

Figure 6:
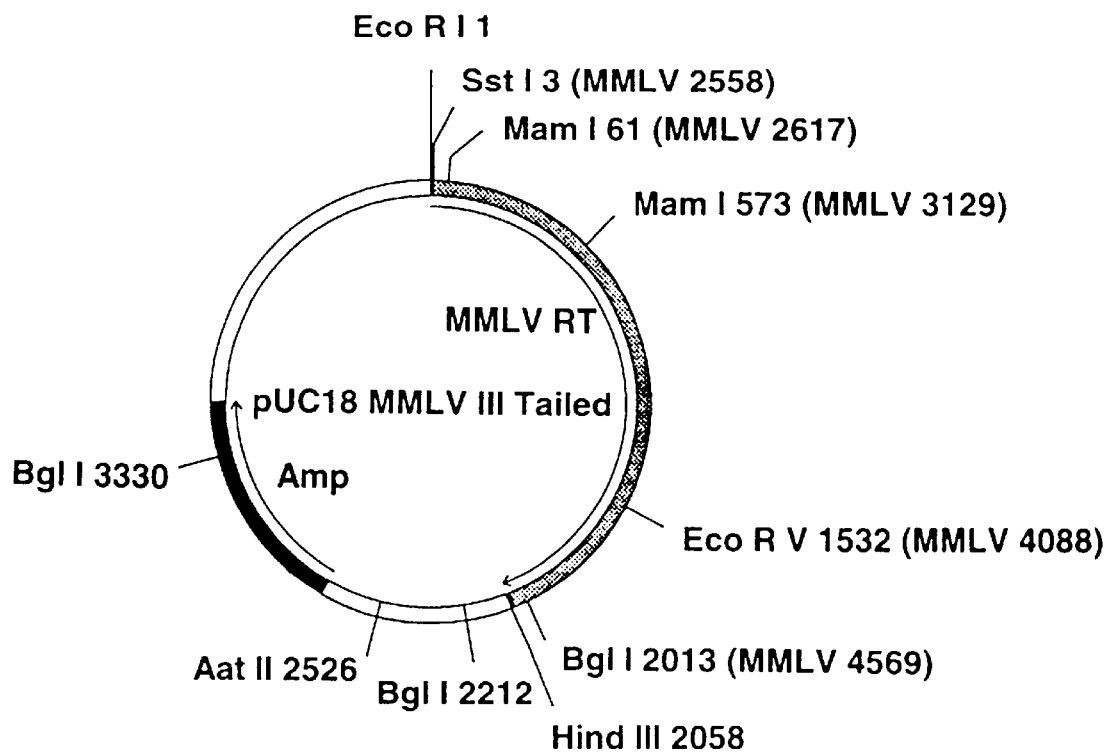
FIG. 6 shows schematically the sequences used in construction of plasmid "pUC18 MMLV III Tailed" using the same nomenclature and designations as used in FIG. 5.

This plasmid was then digested with Eco RI and Bgl I, yielding a 2013 bp fragment of the MMLV-RT gene lacking the terminal 3' sequences of the RT gene. The RT gene fragment was ligated at its Bgl I site to a double-stranded linker designed with Bgl I-Hind III overhangs from two synthetic oligonucleotides, Oligomer #8 and Oligomer #9 (SEQ ID NOS:10 and 11, respectively; FIG. 7). The synthetic linker contained the coding sequences for the carboxyl terminus of MMLV reverse transcriptase and a stop codon. Plasmid pUC18 was digested with Eco RI and Hind III, and the large vector fragment was gel purified and ligated with the reconstructed RT gene. The resulting plasmid was called pUC18 MMLV III Tailed (FIG. 6), and contained the MMLV gene with the extra 3' sequences removed.

C. Construction of pUC18N MMLV Gly and pUC18N MMLV Gly Tet(−)

Figure 8A:
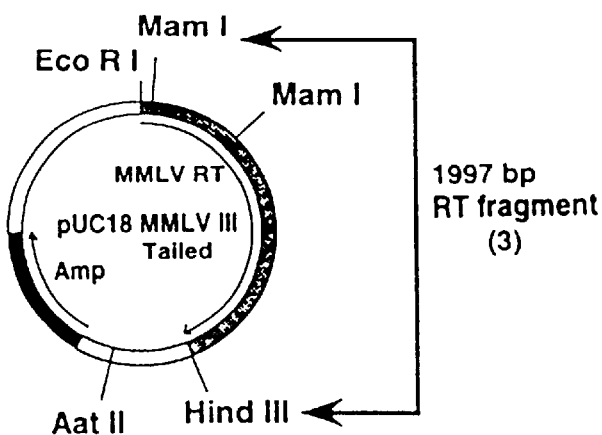
FIGS. 8A to 8F show schematically the construction of plasmids pUC18N MMLV Gly and pUC18N MMLV Gly Tet(−)
Figure 8B:
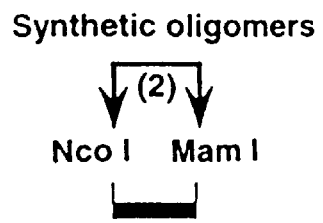

The extraneous 5' sequences of the cloned RT gene were removed as follows. A 1997 bp Mam I-Hind III fragment (fragment (3) in FIG. 8A) was isolated from pUC18N MMLV III Tailed. This nucleic acid fragment (fragment (3)) contained the RT gene without the 5' twenty-three nucleotides of the MMLV-RT gene sequence. Two complementary oligonucleotides (Oligonucleotide #3: CATGGGTCT-GAACATCGAAGATGA (SEQ ID NO:3) and Oligonucleotide #4: TCATCTTCGATGTTCAGACC (SEQ ID NO:4)) were synthesized and hybridized to recreate the 5' portion of the RT gene (fragment (2) in FIG. 8B) but with nucleotides coding for a glycine in the second amino acid position and a Nco I 5' overhang containing an initiation codon, as shown below.

5'-CATGGGTCTGAACATCGAAGATGA-3'
3'-CCAGACTTGTAGCTTCTACT-5'

Figure 8C:
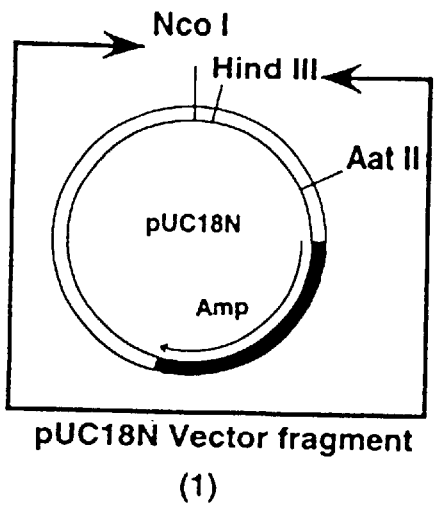
Figure 8D:
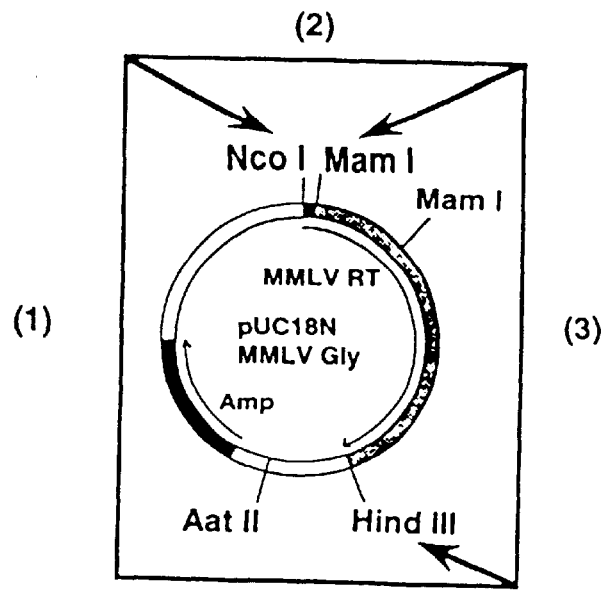
Figure 8E:
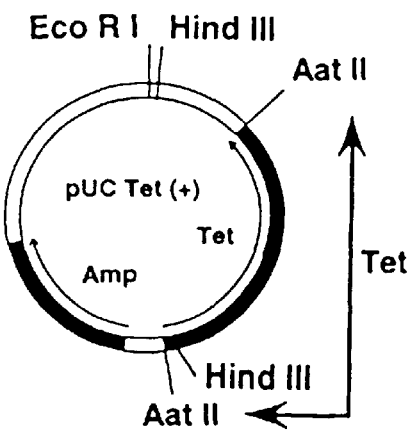
Figure 8F:
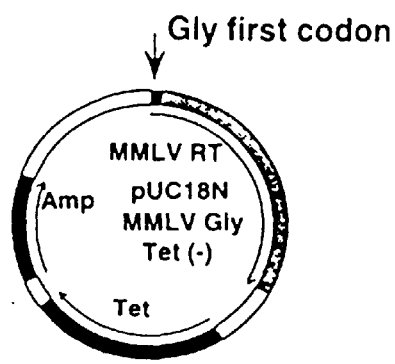

Plasmid pUC18N was digested with Nco I and Hind III (FIG. 8C), and the smaller of the two resulting fragments was removed. The hybridized oligonucleotides (SEQ ID NOS:3 and 4, fragment (2)) were ligated to the larger pUC18N fragment (fragment (1)) at the Nco I site, and the 1992 bp MMLV-RT Mam I-Hind III gene (fragment (3)) was then inserted as well, yielding the expression vector pUC18N MMLV Gly (FIG. 8D). The Tet gene (FIG. 8E) from pUC18 Tet(+), constructed as described below, was inserted at the Aat II site, and the resulting plasmid was called pUC18N MMLV Gly Tet(−) (FIG. 8F). The minus sign refers to the orientation of the Tet gene within the vector.

The cloned MMLV-RT of the present invention differs from the native enzyme in two respects. First, the codon encoding the threonine residue that occupies position 1 of the native enzyme (the second codon of the RT gene) has been replaced with a glycine codon in the cloned RT of the present invention; secondly, the codons for the leucine, asparagine and isoleucine residues occupying amino acid positions 2, 3 and 4 of the mature native protein sequence were replaced with codons more preferred by *E. coli* (See SEQ ID NO.12). The CTA codon coding for leucine was replaced with degenerate codon CTG; the AAT codon coding for asparagine was replaced with degenerate codon AAC, and the ATA codon coding for IsoLeucine was replaced with degenerate codon ATC (see Wada, K. et al., 1991, *Nucl. Acids Res.* 19(supp.):1981–1986).

d. Construction of Plasmid pUC18N SD9D

To optimize the expression of cloned MMLV-RT, the lac Z ribosome binding site (RBS) of pUC18N was modified to contain nine bases complementary to *E. coli* 16S rRNA, rather than the four such bases present in the pUC18 parent vector. At the same time, plasmids were constructed having spacer regions separating the RBS and the ATG initiation codon by either seven, eight, or nine base pairs, as shown for one of the strands in FIG. 3 as SD7, SD8 and SD9, where "a/t" refers to either A or T residues. Common elements in the design of these spacer sequences were: 1) adenine (A) in the third position 5' to the ATG initiation codon, 2) no guanine (G) or cytosine (C) in the spacer region except in the Nco I site, and 3) a 5'-RRTTTRR-3' sequence spanning the RBS and the spacer, where T is thymine and R is a purine nucleotide. These common elements for heterologous gene expression were known (Jay et al., 1981, *Proc. Natl. Acad.*

Sci. USA 78: 5543–48; Jespers et al., 1991, *Protein Engineering* 4: 485–92).

Oligonucleotides used to introduce these modifications are shown in FIG. 4. Oligo # 5, Oligo #6 and Oligo #7 (SEQ ID NOS:5, 6 and 7, respectively) were each used in conjunction with Oligo # 1 (FIG. 2; SEQ ID NO:1). The nucleotides indicated by "at" in a box in FIG. 4 for oligonucleotides 6 and 7 were synthesized with a mixture of A and T because neither was theoretically preferred (see Jespers et al., 1991, *Protein Engineering* 4: 485–92). As in the construction of pUC18N, a 30 bp region of complementarity existed between Oligo #1 and each of Oligo #5, Oligo #6 and Oligo #7. As described above, each pair of oligonucleotides was allowed to hybridize, was filled in using the Klenow fragment of *E. coli* DNA polymerase I, digested with Pvu II and Eco RI and inserted into the same large pUC18 Pvu II-Eco RI fragment used in constructing pUC18N (FIG. 1A). The MMLV-RT gene was then cloned into this vector as a Nco I-Hind III fragment as described below.

These constructs were evaluated by measuring the levels of MMLV-RT expression. The cells containing the plasmid with the 9-base spacer (SD9; made with Oligo #7) displayed the highest level of reverse transcriptase expression. The plasmid was isolated and sequenced; both of the degenerate nucleotides 4 and 5 bases on the 5' side of the ATG start codon were found to be adenosine (A) residues. The expression vector was named pUC18N SD9D (FIG. 9B).

e. Insertion of the Tetracycline Resistance Gene

The ampicillin resistance (β-lactamase) gene of pUC18 was used as a selectable marker gene in the early vector constructions. However, because β-lactamase destroys the antibiotic relatively quickly, there may be a sizable plasmid-minus revertant population in a culture in which ampicillin is the sole selective criterion.

To tightly regulate the cell population in the cultures, the vector was modified to contain a tetracycline resistance gene. Because tetracycline blocks cellular uptake of the antibiotic rather than inactivating it, the culture should be more stable in the presence of tetracycline than with ampicillin.

The tetracycline resistance gene was isolated from pBR322 as a 1427 bp Eco RI-Ava I fragment. The single strand overhangs were filled in using the Klenow fragment of *E. coli* DNA polymerase I, yielding a blunt-ended fragment. Aat II linkers were ligated to the tetracycline resistance gene fragment, and digested with Aat II. Plasmid pUC18 was digested with Aat II, and the linearized vector was ligated to the Aat II fragment containing the tetracycline resistance gene. The ligation mixture was used to transform competent *E. coli* JM109 cells, and the transformants were selected by tetracycline resistance. The structure of the plasmid was verified by restriction mapping. Clones were selected having the tetracycline resistance gene inserted in both orientations; the plasmids were named pUC Tet(+) and pUC Tet(-).

The two plasmids were used as a supply of the tetracycline resistance gene ("Tet") for insertions into plasmids containing cloned MMLV RT. This approach was preferable to inserting the RT gene into a vector already containing the Tet gene, because the Tet gene contains restriction endonuclease recognition sequences for enzymes used in RT gene cloning, while the RT gene contains no Aat II sites.

f. Construction of pUC18N SD9D MMLV Gly and pUC18N SD9D MMLV Gly Tet(-)

Figure 9A:
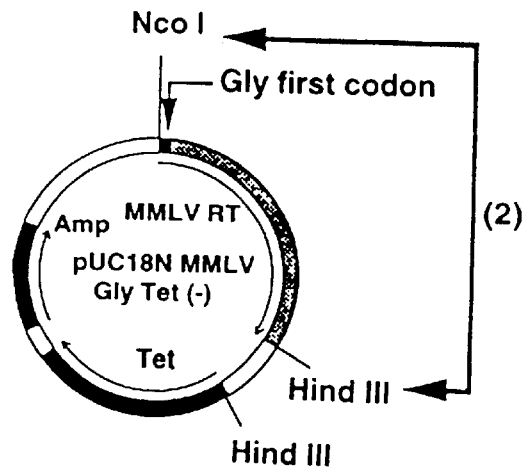
FIGS. 9A to 9E show schematically the construction of plasmids pUC18N SD9D MMLV Gly and pUC18N SD9D MMLV Gly Tet(−)
Figure 9B:
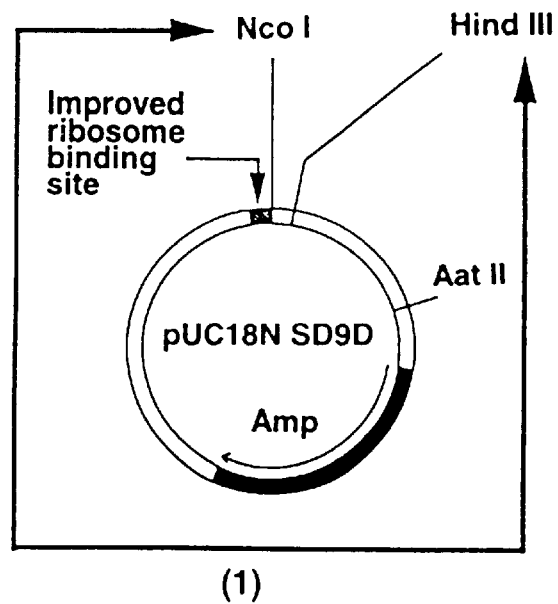
Figure 9C:
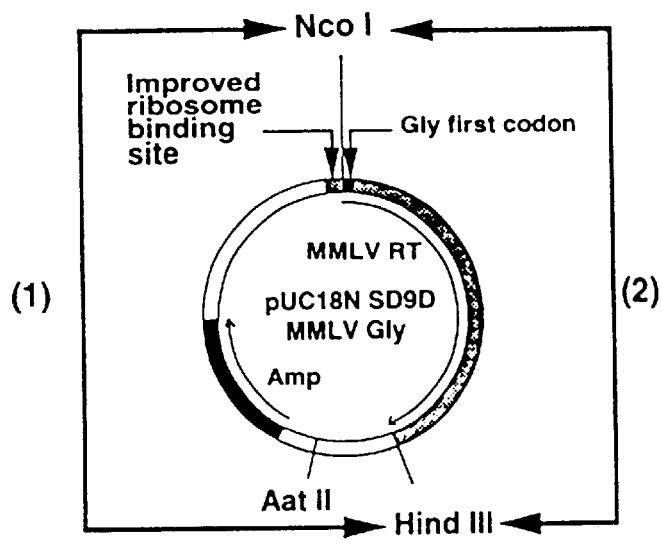
Figure 9D:
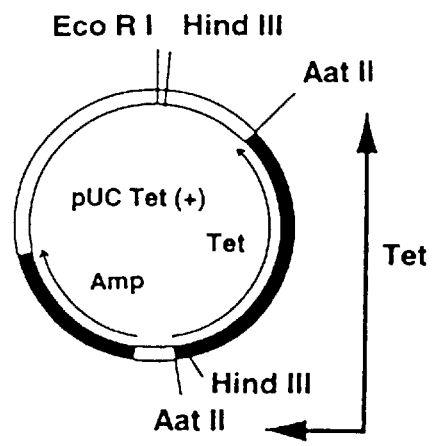
Figure 9E:
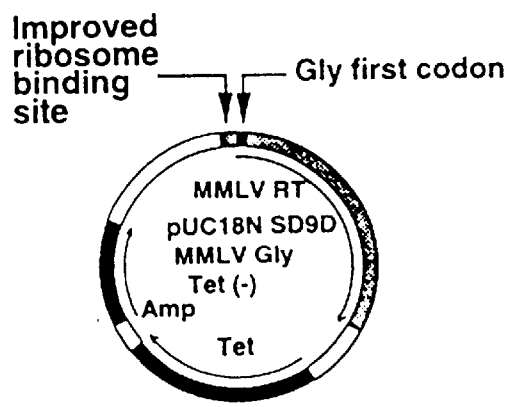

The intact, modified reverse transcriptase gene from pUC18N MMLV Gly Tet(-) was isolated as a 2018 bp Nco I-Hind III fragment (fragment (2) of FIG. 9A) and ligated with vector pUC18N SD9D from which the Nco I-Hind III polylinker region had been removed (fragment (1) of (FIG. 9B). The resulting plasmid, called pUC18N SD9D MMLV Gly (FIG. 9C), contained the MMLV-RT gene modified in the three ways described above in addition to having the improved ribosome binding site and spacer region, as described above. This plasmid was cleaved at its unique Aat II site, and the Aat II Tet gene fragment (FIG. 9D) from pUC18 Tet(+) was inserted into the vector and ligated. Plasmids containing the Tet gene insert were isolated in both possible orientations, and the level of RT expression was tested for clones containing each plasmid. The clone having the Tet gene in the (-) orientation (with the Tet coding strand in the same orientation as MMLV-RT; FIG. 9E) was found to produce higher levels of RT than the clone having the Tet gene in the opposing orientation and was therefore chosen as the preferred clone.

II. Selection of the Host Cell Strain

The following *E. coli* strains were tested for expression and purification of MMLV-RT: JM109, DH5αf', XL1BLUE STRATAGENE®, San Diego, Calif.), JM105, ER 1458, NM 522, In αf'(Invitrogen, San Diego, Calif.), TOPP™ strains 1–6 (STRATAGENE®), 1200, MRE 600, Q13, and A19. Some of these strains (1200, MRE 600, Q13, and A19) are mutants that have reduced levels of RNase I (referred to as "RNase I deficient") compared to wildtype strains (Durwald et al., 1968, *J. Mol. Biol.* 34:331–346; Clark, 1963, *Genetics* 48:105–120; Gesteland, 1966, *J. Mol. Biol.* 16:67; Reiner, 1969, *J. Bacteriol.*97:1522), while others are common laboratory strains. Some of these strains contain the lac I$^q$ repressor and required use of isopropylthiogalactoside (IPTG) to induce transcription. The level of RT expression of host cells containing the RT gene was estimated by visualizing the resulting proteins on SDS-polyacrylamide gels and also, in most cases, by enzyme activity assays on crude cell lysates. Of the RNase I deficient strains, *E. coli* 1200 (Strain 4449, available from the *E. coli* Genetic Stock Center, Yale University) consistently showed high levels of enzyme expression using these assays; unless indicated otherwise, all experiments described herein were conducted using this strain.

Those skilled in the art will appreciate that a number of known and available *E. coli* strains contain mutations that render the strains RNase I deficient compared to wildtype strains (i.e., having about 0.1% or less of wild-type RNase I activity). Known strains having reduced RNase I activity that may serve as alternative heterologous host cells for the recombinant DNA constructs of the present invention include, for example, GM215 (Arraj & Marinus, 1983, *J. Bacteriol.* 153:562–565;), D10 (Gesteland, 1966, *J. Mol. Biol.* 16:67), 2S142 (Chaney, 1977, *Biochemistry* 16:3603), AB301–105 (Kindler, 1973, *Mol. Gen. Genet.* 126:53), 1113B (Castles, 1968, *Biochem. Biophys. Res. Commun.* 32:715; Weatherford, 1972, *J. Biol. Chem.* 247:5404), FS242 (Zimmerman et al., 1973, *Proc. Natl. Acad. Sci. USA* 70:71–75), PR7, PR13, PR27, PR100 and AT9 (Reiner, 1969, *J. Bacteriol.* 97:1431 and *J. Bacteriol.* 97:1437–1522), N464 (Weatherford, 1972, *J. Biol. Chem.* 247:5404), CLB7 (Bassett, 1983, *J. Bacteriol.* 156:1359) and DK533 (Srivastava et al., 1992, *J. Bacteriol.* 174:56–62), all of which are available from the *E. coli* Genetic Stock Center (Yale University, New Haven, Conn.).

III. Growth of *E. coli* 1200 Containing pUC18N SD9D MMLV Gly Tet(-)

The fermentation culture medium (A-Z Amine medium) contained the following components in a volume of 200 liters: 2 kg of N-Z Amine A (Sheffield Products, Norwich, N.Y.), 1 kg Yeast Extract (DIFCO®), 1 kg NaCl, 8 g NaOH and 200 ml Tetracycline (12 mg/ml in 70% ethanol). The mixture was autoclaved in the fermentation vessel at 121° C. for 20 min, then allowed to cool. Tetracycline was added when the temperature reached 37° C.

The inoculum of E. coli 1200 containing pUC18N SD9D MMLV Gly Tet(–) was prepared by inoculating 2 ml of N-Z Amine plus 12 µg/ml tetracycline ("LB+Tet") with a frozen stock culture of the vector-containing strain and shaking overnight at 37° C. The resulting 2 ml culture was used to inoculate 20 one-liter cultures, that were incubated overnight at 37° C. with shaking to produce seed culture.

A 200-liter fermenter was then inoculated with the 20 liters of seed culture, and the cells were grown at 37° C. until 30 min after the culture had reached maximum density as determined by measuring light attenuation at a wavelength of 660 nm. This generally occurs about 7.5 hours after inoculation. During incubation the culture was stirred continuously at 150 RPM for the initial 3 hr and then at 180 RPM thereafter. The vessel was sparged with air at 45 l/min. The pH of the medium was not controlled during fermentation, and rose during that time to approximately 8.2.

The culture was chilled to 20° C., and the cells were collected by centrifugation in a SHARPLES™ centrifuge. The cells were not washed. The cell paste was divided into 200 g portions and frozen in liquid $N_2$. During freezing, the cell mass was broken into smaller pieces to ensure rapid and thorough freezing. The frozen cell paste was then stored at –70° C.

IV. Purification of MMLV RT from E. coli 1200/pUC18N SD9D MMLV Gly Tet(–)

1. Assay of Reverse Transcriptase Activity and Protein Concentration

Methods for assaying RT activity are known in the art. For the work described here, the dT:rA assay described by Kacian was used (1977, "Methods for Assaying Reverse Transcriptase" in Methods in Virology, pp. 143–184 (Academic Press)), in which one unit of reverse transcriptase activity converts 1 nmole of dTTP to acid-precipitable form in 10 min.

2. Cell Lysis

Frozen cell paste (1100 g) was broken into pieces and suspended in 3.3 liters of Lysis Buffer (25 mM Tris-HCl (pH 7.5), 10 mM ethylenediamine tetraacetic acid (EDTA), 10% (v/v) glycerol, 5 mM dithiolthreitol (DTT), 1% (v/v) TRITON® X-100(t-octylphenoxypolxethoxyethanol), 10 mM NaCl, 1 mM phenylmethylsufonyl fluoride (PMSF)) by a stirring at 4° C. Cells were then lysed by 2 passes through an APV GAULIN™ 15MR homogenizer at 8,000 psi continuous pressure. The receiving vessel was kept in an ice water bath, and the initial homogenate was allowed to chill for 30 min before the second pass. The lysate was cleared by centrifugation at 4,500×g for 1 hr at 4° C., and the pellet was discarded. The clarified lysate was either used immediately or stored frozen at –70° C. and brought to 4° C. before use.

3. Phosphocellulose Column Chromatography

Phosphocellulose (WHATMAN®) P11, 100 g) was treated with 2.5 liters of 0.5 N NaOH, followed by 2.5 liters of 0.5 N HCl, as recommended by the manufacturer. After a water wash, the phosphocellulose was suspended in 1.0 liter of 1.0 M Tris-HCl (pH 7.5), allowed to stand for 5 to 10 min, and transferred to a Buchner funnel where buffer was removed by vacuum filtration, and the phosphocellulose was washed with 1.0 M Tris-HCl (pH 7.5) until the effluent pH equaled the wash solution pH. The phosphocellulose was transferred to a beaker and suspended in 1.0 liter of column buffer (25 mM Tris-HCl (pH 7.5), 1 mM EDTA, 10% (v/v) glycerol, 1 mM DTT, 0.1% (v/v) TRITON® X-100 and 1 mM PMSF) containing 0.05 M NaCl. After 5 to 10 min, the buffer was removed by vacuum filtration. Then the phosphocellulose was suspended in 700 ml column buffer containing 0.05 M NaCl, cooled to 4° C., and all subsequent steps were performed at 4° C.

Chromatography was performed using PHARMACIA® FPLC equipment; a column (PHARMACIA® XK 50/30, 5.0 cm×26.0 cm) was packed with the washed and equilibrated phosphocellulose to give a bed of 500 ml. The column was washed with 1 liter of column buffer containing 0.05 M NaCl at a flow rate of 60 ml/hr. Column adapters (Pharmacia® AK 50) minimized the dead volume at the column ends. Clarified cell lysate (600 ml) was applied to the column at a flow rate of 30 ml/hr; then the column was washed with 650 ml of column buffer containing 0.2 M NaCl at the same flow rate. Because of column bed shrinkage, excess buffer was removed from the space above the column bed, and the top flow adapter was readjusted to maintain contact with the bed surface. The column was eluted with a 1500 ml linear salt gradient, from 0.2 M NaCl to 0.7 M NaCl in a column buffer at 30 ml/hr. Effluent was monitored for the presence of protein by its absorbance at 280 nm; 25-ml fractions were collected except during elution of the protein peak, when 15-ml fractions were collected.

Column elution fractions were analyzed using SDS-polyacrylamide gel electrophoresis (SDS-PAGE) followed by Coomassie Brilliant Blue staining.(Laemmli U. K., 1970, Nature 227:680). From each column fraction, 10 µl was analyzed in a gel lane. A control gel lane contained a known amount of purified MMLV-RT. Fractions containing a significant amount of protein migrating with an apparent molecular weight similar or identical to that of the MMLV-RT control and that contained little visible contaminating protein were pooled. Approximately 95% of the protein eluting in the major protein peak was pooled without including a significant amount of contaminating proteins. Well-known enzyme activity assays may also be used to locate the peak MMLV-RT enzyme fractions for pooling.

4. SEPHACRYL™ S200 Gel Filtration

The pooled fractions eluted from phosphocellulose (80 to 100 ml), were concentrated to less than 25 ml by ultrafiltration in an AMICON® ultrafiltration cell using an AMICON® P30 membrane at 20 psi of nitrogen. Two columns (PHARMACIA® XK 26/100, 2.6 cm×94 cm) were packed with SEPHACRYL™ 200 (cross-linked copolymer) of ally dextran and N,N-methylenebisacrylamine (PHARMACIA®) according to the manufacturer's directions. Column adapters minimized the dead volume and the two columns were connected in series. The columns were washed with 2 liters of column buffer containing 0.2 M NaCl at a flow rate of 90 ml/hr. The concentrated pooled fractions (about 25 ml) were loaded onto the upstream column, and the column was developed with the same buffer at a flow rate of 90 ml/hr. Effluent was monitored for its absorbance at 280 nm; the initial 200 ml of effluent was collected in a single pool, and 4-ml fractions were collected during elution of the protein peak. MMLV-RT eluted when about 290 to 300 ml of buffer had been applied to the columns.

Fractions were analyzed using SDS-PAGE as described above. From each fraction in the peak region, 3 µl was run in a gel lane and a control lane contained a known mass of purified MMLV-RT. Fractions were pooled that contained a significant amount of protein migrating with the purified MMLV-RT and little visible contaminating protein. Fractions containing predominant bands of a higher apparent molecular weight than purified MMLV-RT were not pooled. Between 95% to 98% of the protein in the major peak eluted from SEPHACRYL™ S200 was pooled. Although assays for reverse transcriptase activity may be used to locate MMLV-RT in the eluted fractions, analysis preferably includes SDS-PAGE to avoid including higher molecular weight contaminants in the pool.

The pooled fractions eluted from SEPHACRYL™ S200 are sufficiently concentrated for most uses. The enzyme can be stored in 50% glycerol at −20° C.

EXAMPLE 1

Expression of MMLV-RT by E. coli Containing pUC18N MMLV Gly Tet(−) or pUC18N MMLV Gly Tet(−) with a Modified Ribosome Binding Site and Spacer Sequences of Different Lengths The MMLV-RT gene containing the glycine amino acid substitution in the first position was evaluated in vector pUC18N and pUC18N with the spacers and modified ribosome binding site described above. All vectors contained the Tet gene and were evaluated in E. coli strain 1200.

Cultures of E. coli 1200 (50 ml) containing either of these two contructs were grown for 16.5 hr at 37° C. with shaking. Aliquots of 0.5 ml were harvested, centrifuged for 2 min in a microcentrifuge, and the supernatants were discarded. Cell pellets were suspended in 0.5 ml of a wash buffer (50 mM Tris-HCl, pH 8.0, 10 mM NaCl, 5 mM EDTA and 0.25 M sucrose) and centrifuged as before. Cell pellets were frozen at −80° C. and then suspended in 200 µl of lysis buffer (10 mM Tris-HCl, pH 8.0, 10 mM NaCl, 1 mM EDTA, 1% glycerol, 5 mM DTT, 0.2 mM PMSF and 100 µg/ml lysozyme) and left on ice for 20 min; then 100 µl of 0.75% (v/v) TRITON® X-100 was added to each sample, and the mixture was frozen and thawed twice. Lysates were cleared by centrifugation, and total protein was assayed (Read & Northcote, 1981, *Anal. Biochem.* 116:53–64).

Lysate aliquots were assayed for RT activity space (as described by Kacian, 1977, *Methods in Virology*, pp. 143–184). The level of RT activity in each clone was calculated in terms of units per µg of total protein in the lysate, as well as units per ml of bacterial culture. The results shown in Table 1 indicate that the vector containing the modified ribosome binding site (RBS) and the nine-base spacer sequence expressed the highest levels of RT enzyme.

TABLE 1

Comparison of RT Expression in Different Plasmid Constructs

| Expression Vector | RT Activity (U/µg Total Protein) | RT Activity (U/ml Culture) |
|---|---|---|
| Unmodified pUC18N | 1.81 | 746 |
| pUC18N with 7-base spacer and improved RBS | 2.25 | 823 |
| pUC18N with 8-base spacer and improved RBS | 1.72 | 679 |
| pUC18N with 9-base spacer and improved RBS | 2.69 | 1,036 |

EXAMPLE 2

Comparison of Modified MMLV-RT in E. coli 1200 and JM 109 Host Strains

Plasmid pUC18N was used to create plasmids encoding MMLV-RT with glycine, alanine, or valine substitutions in the first native amino acid position. These substitutions were created using oligonucleotides similar to oligos 3 and 4, but with a codon of sequence 5'-GTT-3' or 5'-GCT-3'(coding for valine or alanine respectively) in the second position of the RT gene, following the initiation codon. The Tet gene from pUC18 Tet(+) was inserted into the resulting plasmids in each orientation for comparison. These plasmids were used to transform E. coli JM109 host cells that contain an episomal copy of the lac repressor lac I$^q$ gene. The transformant cells were grown overnight as in Example 1, except when the cells reached log phase growth, the lac promoter was induced by addition of 0.5 mM IPTG for about 22 hr. Aliquots were harvested and assayed for RT activity as in Example 1. The results in Table 2 show that the Gly Tet(−) construction produced the highest level of RT enzyme expression.

TABLE 2

Effect of Orientation of Tet gene on RT Activity

| | RT Activity (U/µg Total Protein) | RT Activity (U/ml Culture) |
|---|---|---|
| Gly Tet (+) | 0.44 | 177 |
| Gly Tet (−) | 1.29 | 472 |
| Ala Tet (+) | 0.59 | 229 |
| Ala Tet (−) | 0.54 | 243 |
| Val Tet (+) | 0.91 | 400 |
| Val Tet (−) | 1.03 | 395 |

In a separate experiment, the Gly Tet(−) and the Val Tet(−) constructs were evaluated in E. coli host strains 1200 and JM 109. The JM 109 cultures were IPTG induced as above, while the 1200 cultures were uninduced. The results in Table 3 show that the levels of expression in both strains are comparable for the Gly-substituted MMLV-RT, and higher in strain 1200 for the Val-substituted plasmid.

TABLE 3

Comparison of RT Expression in Different Host Cell Strains

| Host cell/ plasmid | RT Activity (U/µg Total Protein) | RT Activity (U/ml Culture) |
|---|---|---|
| 1200/Gly Tet (−) | 1.04 | 591 |
| JM 109/Gly Tet (−) | 1.05 | 533 |
| 1200/Val Tet (−) | 1.00 | 516 |
| JM 109/Val Tet (−) | 0.61 | 357 |

EXAMPLE 3

Growth of E. coli 1200/pUC18N SD9D MMLV Gly Tet(−) and Expression of MMLV-RT In this example, 1 liter of autoclaved growth medium contained 10 g of N-Z Amine A, 5 g of yeast extract, 5 g of NaCl, and 0.1 ml of 10 N NaOH; and 1 ml of 12 mg/ml tetracycline in 70% ethanol was added to the cooled, autoclaved medium.

Medium (2 ml) was inoculated from a frozen stock culture of the E. coil transformant and cells were grown overnight with shaking at 37° C. The 2-ml bacterial culture was inoculated into 500 ml of medium, and this culture was grown overnight as above. The 500-ml culture was inoculated into 5 liters of medium in a fermentor (NEW BRUNSWICK BIOFLO™III) and the culture was grown at 37° C. with stirring at 350 RPM, sparged with air at 4 liters/min. Samples (5 to 10 ml) were taken hourly for measurement of pH, optical density ($A_{600}$), protein concentration (mg/ml) and reverse transcriptase activity (units per assay and units per mg of protein). These results are shown in Table 4.

TABLE 4

Growth Kinetics of 1200/pUC18N SD9D MMLV Gly Tet(−)

| Sample | Time (hr) | pH | A600 | Protein (mg/ml) | RT Activity (U/Assay) | RT Activity (U/mg Protein) |
|---|---|---|---|---|---|---|
| 1 | 0 Pre-inoculation | 6.93 | 0.00 | 0.00 | 0.00 | 0 |
| 2 | 0 Post-inoculation | 7.15 | 0.29 | 0.06 | 1.17 | 2920 |
| 3 | 1 | 7.14 | 0.22 | 0.18 | 0.91 | 2270 |
| 4 | 2 | 6.97 | 0.69 | 0.07 | 0.51 | 1270 |
| 5 | 3 | 6.91 | 0.96 | 0.11 | 0.87 | 2170 |
| 6 | 4 | 7.02 | 1.72 | 0.09 | 0.92 | 2300 |
| 7 | 5 | 7.40 | 2.16 | 0.13 | 0.60 | 1510 |
| 8 | 6 | 7.70 | 2.50 | 0.11 | 1.27 | 3180 |
| 9 | 7 | 7.83 | 2.91 | 0.12 | 1.49 | 3720 |
| 10 | 8 | 7.98 | 2.79 | 0.09 | 1.46 | 3660 |

EXAMPLE 4

Large-Scale Purification of Cloned MMLV-RT

The enzyme was prepared as described above and in Example 1 with volumes of reagents adjusted in proportion to the weight of the pelleted cells at the beginning of the procedure. As indicated in Table 5, highly purified RT enzyme was recovered with a 48% yield.

TABLE 5

Purification Parameters: MMLV-RT Purification Scale-Up

| Fraction | Volume (ml) | Protein (mg) | Total Activity (U) | Specific Activity (U/mg) | Yield (%) |
|---|---|---|---|---|---|
| Crude Lysate | 605.6 | $2.1 \times 10^4$ | $1.5 \times 10^8$ | 7,100 | 100 |
| P11 Pool | 15.2 | 741 | $8.2 \times 10^7$ | 110,656 | 52 |
| SEPHACRYL ™ Pool | 79 | 363 | $7.9 \times 10^7$ | 217,400 | 48 |

EXAMPLE 5

Figure 10:
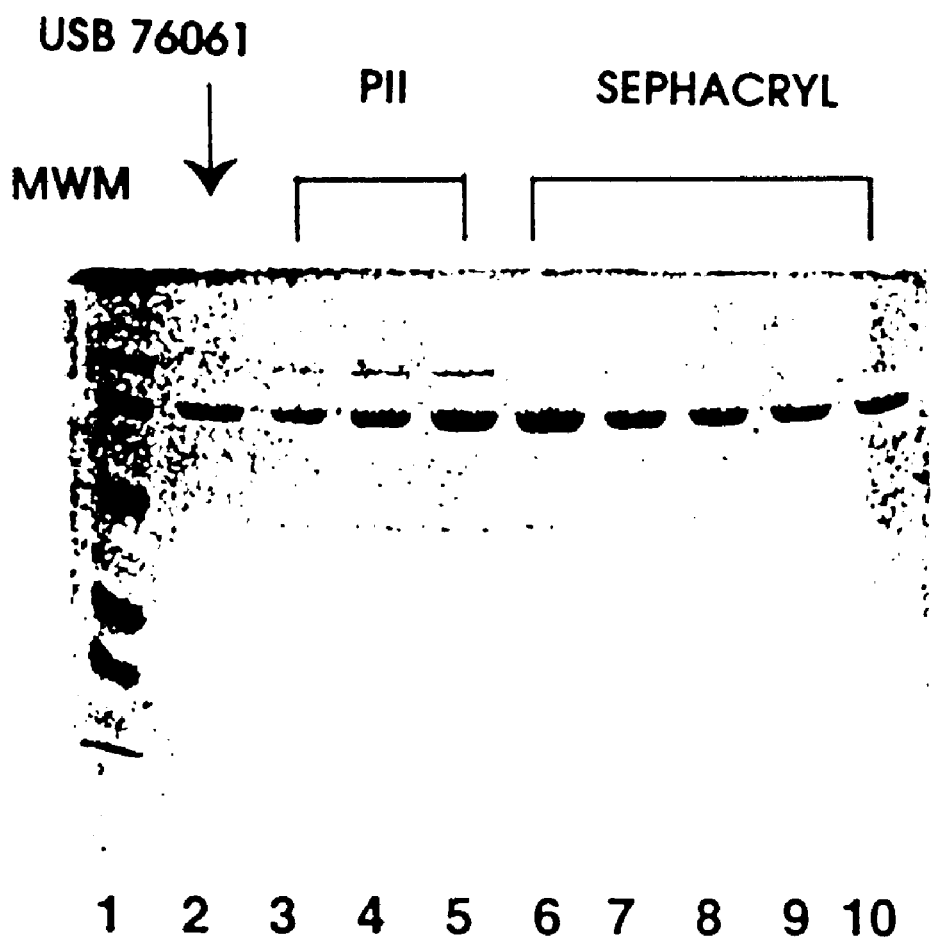
FIG. 10 shows a photocopy of a sodium dodecyl sulfate polyacrylamide gel electrophoresis (SDS-PAGE) gel showing molecular weight markers ("MWM", lane 1); a commercially available RT preparation ("USB 76061", lane 2); and P11 fractions (lanes 3 to 5) and Sephacryl™S-200 fractions (lanes 6 to 10) containing purified MMLV-RT of the present invention.

SDS-PAGE of Purified MMLV-RT from *E. coli* 1200/pUC18N SD9D MMLV Gly Tet(−) Clone Purification progress was monitored by SDS-PAGE analysis of protein in the pooled fractions from phosphocellulose column chromatography ("P11 pool") and the pooled fractions from SEPHACRYL™ S200 gel filtration ("SEPHACRYL™ pool") of Example 4. SDS-PAGE was conducted in a 10% reducing gel (essentially as described by Laemmli U. K., 1970, *Nature* 227:680), loaded as shown below. Samples were prepared as follows. An aliquot of the P11 pool was diluted 50-fold into a gel sample buffer (50 mM Tris-HCl, pH 6.8, 10% (v/v) glycerol, 5% β-mercaptoethanol (BME), 2;% (w/v) SDS and 0.05% (w/v) bromphenol blue) and heated at 95° C. for 5 min. An aliquot from the SEPHACRYL™ pool was diluted 10-fold with gel sample buffer and heated in the same way. A sample of commercially obtained MMLV-RT (U.S. Biochemicals, Cleveland, Ohio) was prepared identically; as supplied, this sample had a specific activity of 187,000 U/mg and an initial concentration of 1500 U/μl. Prestained molecular weight markers (BIO-RAD™ Laboratories, San Rafael, Calif.) were used to estimate the molecular weights of the proteins. The apparent molecular weights of the marker proteins were: 18,500 Da (egg white lysozyme), 27,500 Da (soybean trypsin inhibitor), 32,500 Da (bovine carbonic anhydrase), 49,500 Da (chicken ovalbumin), 80,000 Da (bovine serum albumin), and 106,000 Da (rabbit muscle phosphorylase B). A photocopy of the gel is shown in FIG. 10.

| Order of SDS-PAGE Samples in MMLV-RT Purification | | |
|---|---|---|
| Lane | Sample | Volume (μl) |
| 1 | Molecular Weight Markers (MWM) | |
| 2 | Commercial RT preparation | |
| 3 | P11 Pool | 2.0 |
| 4 | P11 Pool | 4.6 |
| 5 | P11 Pool | 7.0 |
| 6 | P11 Pool | 10.0 |
| 7 | Sephacryl ™ Pool | 6.5 |
| 8 | Sephacryl ™ Pool | 5.0 |
| 9 | Sephacryl ™ Pool | 4.2 |
| 10 | Sephacryl ™ Pool | 3.3 |

EXAMPLE 6

Contaminating Ribonuclease Activity in a Commercial Preparation of MMLV-RT

A 24 cm×0.4 cm column of SEPHADEX™ G-75 (beads of dextran cross-linked with epichlorohydrin was equilibrated with 1×Column Buffer (20 mM Tris-HCl, pH 7.6, 0.1 mM EDTA, 200, mM NaCl, 1 mM DTT, 0.01% (v/v) NON P-40™ ((Octylphenoxy)-Polyethoxyethanol and 10% (v/v) glycerol).

RNase assays were performed by using nucleic acid hybridization to measure loss of RNA in a sample incubated with the enzyme substantially, using previously described hybridization and detection methods U.S. Pat. No. 5,283,174 to Arnold et al.; U.S. Pat. No. 5,824,475 to Nelson et al.). From each enzyme samples, 5 μl were transferred to a test tube and 10 μl of an in vitro synthesized RNA transcript about 1–4 fmol) in water were added; the reactions were incubated at 37° C. for 1 hr. An acridinium ester-labelled DNA probe complementary to a region of the RNA transcript was added in 50 μl of 0.1 M lithium succinate, pH 4.7, 1.1 M lithium chloride, 2% (w/v) lithium lauryl sulphate, 20 mM EDTa, 20 mM ethylene glycol bis(beta-amino ethyl ether) N,N,N$^1$,N$^1$ tetraacetic acid (EGTA), and 15 mM ALDRITHIOL™ (2,2'-dipyridyldisulfido, 2,2'-dipyridylpyridne Chemical Company, Milwaukee, Wis.), and the reaction mixture was incubated at 60° C. for 20 min. Then, 300 μl of a solution of 0.6 M sodium borate (pH 8.5), 1% (v/v) TRITON® X-100 were added, and the reaction mixture was incubated at 60° C. for 7 min to destroy acridium ester present on unbound probe. The amount of remaining label was determined in a luminometer (LEADER™, Gen-Probe Inc., San Diego, Calif.), detected as relative light units ("RLU").

Methods for assessing RNase activity using radiolabeled probes or directly measuring degradation of radiolabelled RNA by monitoring conversion from acid-precipitable to acid soluble forms, or other methods are well known to those skilled in the art and may be used for assaying low level RNase activity.

A commercial preparation (25 μl) of MMLV-RT (U.S. Biochemicals, Cleveland, Ohio) was mixed with 12.5 μl of 10×Column Buffer without glycerol, 10 μl of a 10 mg/ml solution of Blue Dextran, and 77.5 μl water. Before use, the water was treated with diethyl pyrocarbonate to destroy contaminating RNases (see Sambrook et al., 1989, *Molecular Cloning: A Laboratory Manual* (2d ed., Cold Spring Harbor Laboratory Press, Cold Spring Harbor, N.Y.)). The enzyme was applied to the column and eluted with Column Buffer at a flow rate of 1.8 ml/hr. Fractions (230 μl) were collected and assayed for reverse transcriptase and RNAse activities, as described above.

The results of two identical column runs are shown in Table 6; fractions that were not assayed are not listed in the table.

TABLE 6

Comparison of Enzyme Activities For Two Different Column Runs

| | Column 1 | | Column 2 | |
|---|---|---|---|---|
| Fraction | RT Activity (RLU) | RNAse Activity (% degraded) | RT Activity (RLU) | RNAse Activity (% degraded) |
| 2 | 61 | | | |
| 4 | 1000 | | | |
| 6 | 2574 | | | |
| 8 | 1751 | | 1605 | |
| 9 | | | 20029 | |
| 10 | 14328 | 14 | 98216 | 9 |
| 11 | | | | |
| 12 | 143493 | 0 | 40619 | 0 |
| 13 | | | 43523 | |
| 14 | 21570 | 51 | 9299 | 55 |
| 15 | | | 26650 | |
| 16 | 11306 | 0 | 13490 | 17 |
| 17 | | | 1226 | |
| 18 | | | 4713 | |
| 19 | | | 1462 | |
| 20 | 2583 | 64 | 1379 | 57 |
| 21 | | | 1263 | |
| 22 | 913 | 52 | 1072 | 0 |
| 24 | 907 | 21 | | 44 |
| 26 | 887 | 56 | | 73 |
| 27 | | | | |
| 28 | 21375 | | | |
| 30 | 8100 | | | |

As Table 6 illustrates, the commercial enzyme preparation contains significant endogenous RNase activity other than the RNAse H activity associated with the MMLV-RT enzyme, because it degrades single-stranded RNA. When analyzed by gel filtration chromatography, at least four peaks of non-RNase H RNAse activity were obtained. These peaks may represent four distinct enzymes or may represent aggregation of one or more proteins, dissociation of a protein into subunits, or other chromatographic artifacts. At least one of these peaks of non-RNase H RNase activity co-eluted with the MMLV-RT.

EXAMPLE 7

Comparison of Contaminating Ribonucleases in Partially Purified Recombinant MMLV-RT from *E. Coli* Host Cells JM 109 and 1200

To compare the amount of contaminating ribonuclease activities present in MMLV-RT-containing cell lysates after phosphocellulose column purification between host cells JM 109 and 1200 transformed with plasmid pUC18N SD9D MMLV Gly Tet(−), fractions from each column were assayed for reverse transcriptase activity using the dT:rA assay (Kacian, 1977, *Methods in Virology*, pp. 143–184) and for non-RNase H RNase activity using the assay described in Example 6. The results obtained for each cell type are shown in the Tables 7 and 8.

TABLE 7

Enzyme Activity of Enzyme Purified from *E. coli* Strain 1200 Host Cells

| Fraction | RT Activity (RLU) | RNAse activity (% degraded) |
|---|---|---|
| 1 | 1,007 | 0 |
| 5 | 1,084 | 0 |
| 10 | 1,021 | 0 |
| 15 | 3,712 | 0 |
| 20 | 38,359 | 0 |
| 25 | 20,741 | 0 |
| 30 | 316,513 | 0 |
| 33 | 346,922 | 0 |
| 36 | 504,196 | 0 |
| 39 | 387,533 | 0 |
| 42 | 371,897 | 0 |
| 45 | 472,248 | 0 |
| 48 | 1,199,993 | 0 |
| 51 | 1,529,015 | 0 |
| 54 | 1,126,592 | 0 |
| 57 | 1,034,428 | 0 |
| 60 | 850,009 | 0 |
| 63 | 698,462 | 0 |
| 66 | 390,121 | 0 |
| 69 | 177,736 | 0 |
| 72 | 260,049 | 0 |

TABLE 8

Enzyme Activity of Enzyme Purified from *E. coli* Strain JM 109 Host Cells

| Fraction | RT Activity (RLU) | RNAse activity (% degraded) |
|---|---|---|
| 1 | 1,103 | 0 |
| 5 | 1,238 | 0 |
| 10 | 1,287 | 0 |
| 15 | 28,359 | 29 |
| 20 | 50,927 | 75 |
| 25 | 29,551 | 70 |
| 30 | 350,732 | 83 |
| 35 | 198,151 | 30 |
| 38 | 164,047 | 54 |
| 41 | 149,647 | 66 |
| 44 | 161,963 | 62 |
| 47 | 674,123 | 81 |
| 50 | 2,060,603 | 83 |
| 53 | 2,703,286 | 85 |
| 56 | 1,967,435 | |
| 59 | 1,608,490 | 90 |
| 62 | 782,936 | 86 |
| 65 | 265,569 | 78 |
| 68 | 147,948 | 63 |
| 71 | 78,481 | 38 |
| 74 | 44,426 | 3 |
| 77 | 19,964 | 0 |
| 81 | 13,900 | 0 |

The data show that the enzyme prepared from JM 109 cells contained significant amounts of non-RNase H ribonuclease activity throughout the phosphocellulose column profile. Significant amounts of RNase activity eluted with the reverse transcriptase activity. In contrast, the reverse transcriptase purified from *E. coli* 1200 cells was free of detectable contaminating RNase activity after the crude extract was purified by phosphocellulose column chromatography.

EXAMPLE 8

Amplification of *Mycobacterium tuberculosis* Ribosomal RNA (rRNA) Target Sequence Using Purified Recombinant MMLV Reverse Transcriptase From *E. coli* 1200/pUC18N SD9D MMLV Gly Tet(−)

Nucleic acid amplification was performed using a transcription-mediated amplification procedure previously described in detail (Kacian & Fultz, EPO 0 408 295 A2 and U.S. Pat. Nos. 5, 399,491, 5,480,784, 5,824,518 and 5,888, 779). A reagent mixture (Solution A) was made by adding, in order, to 768 μl of water, 25 μl 1 M Tris-HCl (pH 8.0), 50 μl 1 M MgCl$_2$, 44 μl KCl, 500 μl 40 mM rNTPs, 55 μl 10 mM dNTPs, 9 μl T7 promoter-primer (84 pmoles/μl), and 5 μl non-T7 primer (150 pmoles/μl), that was mixed to produce a volume suitable for 50 assays. To each reaction tube was added: 40 μl of Solution A and 10 μl of purified target rRNA (0.05–25 fg/μl diluted in Template Dilution Buffer: 0.2% (w/v) bovine serum albumin in 150 mM NaCl). The target rRNA, prepared using well-known methods, had nucleic acid sequences sufficiently complementary to the primer and the promoter-primer to allow hybridization to occur under stringent hybridization conditions. Onto the surface of each reaction mixture, 200 μl of silicone oil was layered and the reaction tubes were heated at 95° C. for 15 min. Reaction tubes were then transferred to 42° C. and allowed to cool for 5 min.

An enzyme mixture was prepared by transferring 46.8 μl of Dilution Buffer to a tube and adding 1.1 μl (900 U) of MMLV-RT and 2 μl (400 U) of T7 RNA polymerase. Enzyme mixture was added to each reaction tube and the reactions were incubated at 42° C. for 2 hr to allow amplification to occur.

The amount of amplified RNA generated was measured as RLU using an acridinium ester-labeled DNA probe directed to the target sequence as previously described (Arnold et al., PCT Patent Application WO 89/02476; Arnold et al., 1989, *Clin. Chem.* 35:1588–1594). All reactions were run in quadruplicate except for a negative control, which was run in duplicate. The results in Table 9 show that saturating levels of the amplified target sequence were obtained with as little as 2.5 fg of input template RNA at the beginning of the experiment.

TABLE 9

Sensitivity of Enzyme Preparation in an Amplification Reaction

| Amount of Template RNA Added (fg) | Signal (RLU) |
|---|---|
| 250 | 2841164 |
| | 2802308 |
| | 2828732 |
| | 2828837 |
| 25 | 2801357 |
| | 2968585 |
| | 2748909 |
| | 2723562 |
| 2.5 | 2761901 |
| | 2809799 |
| | 2932942 |
| | 2906826 |
| 0 | 2246 |
| | 2443 |

EXAMPLE 9

Synthesis of cDNA Using Purified Recombinant MMLV-RT from *E. coli* 1200/pUC18N SD9D MMLV Gly Tet(−)

The ability of the recombinant purified MMLV-RT to synthesize cDNA was compared to that of a commercially available RT preparation (U.S. Biochemicals) in an RNA sequencing reaction.

TTE buffer was prepared by mixing 20 ml of 1 M Tris-HCl (pH 7.5), 0.4 mM EDTA (pH 8.0) and 281.7 μl triethylamine. Primers had the following sequences:
SEQ ID NO:8 5'-TACCTTGTTACGACTTCACCCCA-3'
SEQ ID NO:9 5'-CTTAGATGCTTTCAGC 3'

Primers were labeled with $^{32}$P at their 5' ends using polynucleotide kinase and well-known nucleic acid end-labelling procedures. The end-labelled primers were purified by chromatography (using NENSORB columns (New England Nuclear) according to the manufacturer's specifications), followed by ethanol precipitation.

Reactions were carried out using either purified recombinant MMLV-RT from *E. coli* 1200/pUC18N SD9D MMLV Gly Tet(−) or reverse transcriptase purchased from a commercial vendor (U.S. Biochemicals).

Reaction mixtures contained the following reagents in a 100 μl final volume: 10 μl of GPE Buffer (500 mM Tris-HCl, pH 7.6, 175 mM MgCl$_2$, 250 mM KCl, 20 mM spermidine), 8 μl of stock rNTPs (25 mM rCTP and rUTP; 65 mM rATP and rGTP), 4 μl of stock dXTPs (10 mM each), 0.5 μl of 1 M DTT, 20 pmoles of $^{32}$P-labelled primer, 20 pmoles of unlabelled primer, 20 pmoles of purified *E. coli* rRNA, and 600 U of reverse transcriptase. In reaction tubes, all components except the reverse transcriptase were mixed and heated at 95° C. for 5 min to denature the template RNA secondary structure. Reactions were then placed at 60° C. for 30 min to allow the primers to anneal to the rRNA target. Reaction mixtures were cooled to room temperature, the reverse transcriptase was added, and DNA synthesis was carried out at 42° C. for 60 min. Reactions were analyzed on 7% polyacrylamide gels essentially as previously described (Williams et al., 1986, *BioTechniques* 4: 138–147).

Both enzymes synthesized cDNA from the RNA template with equal efficiency as judged from the gel electrophoretograms.

EXAMPLE 10

RT-PCR using Recombinant MMLV-RT from *E. coli* 1200/pUC18N SD9D MMLV Gly Tet(−)

All PCR reactions were run in a DNA thermal cycler (Perkin Elmer-Cetus Model 9600) programmed to incubate the reactions as follows: 94° C. for 3 min; 35 cycles each consisting of 51° C. for 30 sec, 72° C. for 2 min and 94° C. for 1 min; 72° C. for 5 min; and 4° C. overnight.

Two separate preparations of recombinant MMLV-RT of the present invention were used for this experiment, and a commercial RT preparation (U.S. Biochemicals). Different amounts of RT were tested, but 50 U of the enzyme was found to be optimum for all enzyme preparations used. Other reagents were: 5×RT Buffer (50 mM Tris-HCl, pH 8.3, 75 mM KCl, 3 mM MgCl$_2$, 5 mM DTT); 10×PCR Buffer (100 mM Tris-HCl, pH 8.3, 500 mM KCl, 15 mM MgCl$_2$, 0.1% gelatin; Perkin Elmer); RT Premix (for each reaction use 4 μl 5×RT Buffer, 0.8 μl of a 25 mM solution of each dNTP, 50 units RT, 100 pmoles (+) sense primer, water in a total volume of 20 μl); PCR Premix (for each reaction use 8 μl 10×PCR Buffer, 100 pmoles (+) sense primer, 2.5 units Taq DNA Polymerase, and water to a total volume of 80 μl. Probes were stored in 10 mM lithium succinate buffer (pH 5.0), 0.1% lithium lauryl sulfate (LLS).

Probes and primers used for this experiment were complementary to sequences of the human papilloma virus (HPV) genome. Probes were labeled with acridinium ester as previously described in detail (Arnold & Nelson, PCT Patent Application No. WO 89/02476).

Crude preparations of unspliced template RNA were made by suspending SiHa cells (which contain HPV nucleic acid sequences integrated into their genome) at a concentration of $1.6 \times 10^7$ cells/ml in 10 mM sodium phosphate (pH 7.6) and 100 mM NaCl. Cells were heated for 15 min at 95° C., cooled to room temperature, and diluted into water to the desired concentration. RNA transcripts from the E6 gene were prepared by in vitro transcription of DNA from a plasmid containing the HPV16 E6 gene. This plasmid was constructed by cloning a DNA fragment from an HPV clone (Matsukura et al., 1986, *J. Virol.* 58:979–982) into PBLU-SCRIPT™ II SK+ and SK– cloning vectors (STRATAGENE®, San Diego, Calif.) and RNA transcripts were prepared using well known methods, as indicated by the manufacturer.

Amplification reactions were conducted as follows. Target nucleic acids were added to the MMLV-RT premix and the mixture was heated at 95° C. for 2 min. Primers were added and allowed to anneal to the target nucleic acids for 10 min at 60° C.; then the reaction mixture was cooled on ice. Reverse transcriptase was added, and reactions were incubated at 37° C. for 30 min. Reactions were heated at 95° C. for 10 min to inactivate the reverse transcriptase, cooled in ice, and two drops of mineral oil were layered onto the surface of reaction mixture. Taq DNA polymerase, diluted into PCR Premix at the concentration indicated above, was added to each sample (80 µl per reaction). Samples were placed in the thermal cycler at 95° C., and cycling was performed as described above.

Hybridization and detection were carried out as previously described (Arnold & Nelson, PCT Patent Application No. WO 89/02476). For each hybridization assay, 30 µl of water was mixed with 10 µl of a PCR reaction mixture. The DNA was denatured at 95° C. for 5 min and 10 µl of diluted probe was added and mixed. Tubes were incubated at 60° C. for 15 min and then 300 µl of selection reagent was added, mixed and incubated at 60° C. for 5 min. Tubes were cooled in ice, and the remaining acridinium ester label was measured as RLU in a LEADER™ luminometer (Gen-Probe Inc., San Diego, Calif.).

The results are shown in Table 10.

TABLE 10

| Copies of Template RNA | RNA Type | Origin of Reverse Transcriptase | Average Net RLU |
| --- | --- | --- | --- |
| $1 \times 10^7$ | SiHa cell lysate | commercial | 423,084 |
| $1 \times 10^7$ | SiHa cell lysate | E. coli 1200/pUC18N SD9D MMLV Gly Tet (–) | 445,003 |
| $1 \times 10^7$ | E6 transcript | commercial | 2,741,628 |
| $1 \times 10^7$ | E6 transcript | E. coli 1200/pUC18N SD9D MMLV Gly Tet (–) |  |
| $1 \times 10^4$ | E6 transcript | commercial | 103,501 |
| $1 \times 10^4$ | E6 transcript | E. coli 1200/pUC18N SD9D MMLV Gly Tet (–) | 1,395,572 |
| $1 \times 10^5$ | E6 transcript | commercial | 1,317,386 |
| $1 \times 10^5$ | E6 transcript | E. coli 1200/pUC18N SD9D MMLV Gly Tet (–) | 2,283,979 |
| $1 \times 10^6$ | E6 transcript | commercial | 1,661,390 |
| $1 \times 10^6$ | E6 transcript | E. coli 1200/pUC18N SD9D MMLV Gly Tet (–) | 2,951,045 |
| $1 \times 10^7$ | E6 transcript | commercial | 2,294,856 |
| $1 \times 10^7$ | E6 transcript | E. coli 1200/pUC18N SD9D MMLV Gly Tet (–) | 2,421,754 |

EXAMPLE 11

Construction of Plasmids Encoding His-tagged MMLV-RT

This example describes construction of recombinant DNA in which codons encoding six histidine residues were added to either the 5' or 3' end of the previously described recombinant MMLV-RT construct, pUC18N SD9D MMLV Gly. The encoded histidine residues are referred to as a "His tag" located at the amino- and carboxy-termini of the MMLV-RT enzyme. For both types of constructs, a fragment containing the His tag and a portion of the MMLV clone was synthesized using PCR by using a pair of primers that each contain a restriction endonuclease recognition sequence and a sequence complementary to the MMLV RT sequence of pUC 18N SD9D MMLV Gly, which was used as a template for PCR amplification. One primer of each pair also contained sequence encoding six histidine residues. Each primer pair was incubated with the template sequence in a PCR amplification mixture and the amplified fragment flanked by the primer sequences was produced. The PCR fragment was then cut with the restriction endonucleases specific for the ends of the amplified fragment and inserted into the appropriate restriction endonuclease sites of a similarly cut vector sequence containing the rest of the MMLV-RT gene sequence (i.e., a large fragment of pUC18N SD9D MMLV Gly from which the small restriction fragment corresponding to the 5' or 3' end of the MMLV RT gene had been removed following restriction endonuclease digestion). The large vector fragment and PCR amplified His-tag containing fragment were ligated and clones were isolated following transformation of an *E. coli* host cell and selection for ampicillin-resistant colonies. Individual clones were isolated and their plasmid DNA purified for DNA sequencing to confirm the sequence of the inserted fragment at the 5' or 3' end of the MMLV RT gene.

Figure 11:
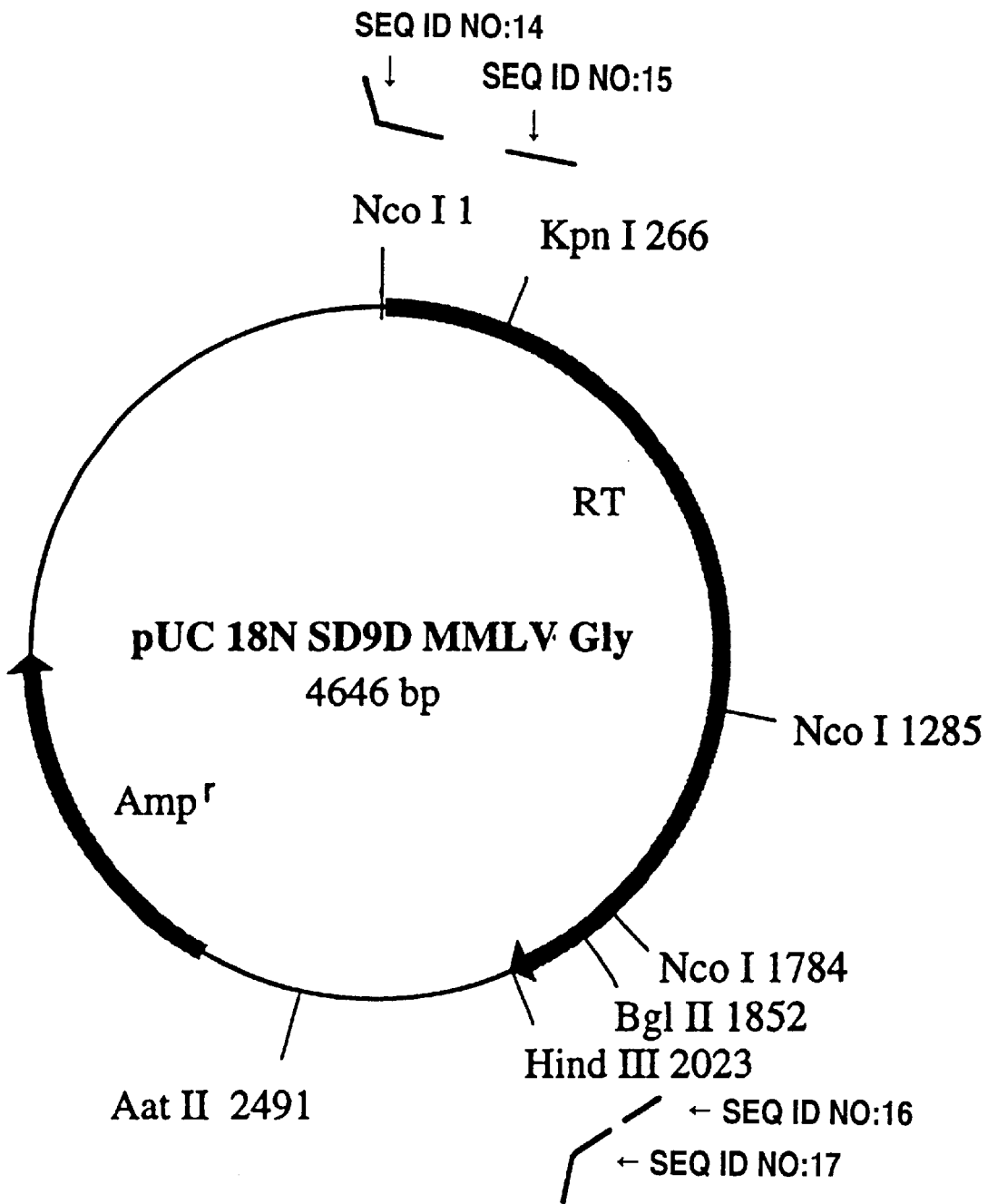
FIG. 11 shows the relative locations of primers having SEQ ID NO:14, SEQ ID NO:15, SEQ ID NO:16 and SEQ ID NO:17 compared to plasmid pUC18N SD9D MMLV Gly; the primers were used to amplify fragments that were cloned into a part of pUC18N SD9D MMLV Gly to introduce His-tag codons into the 5' and 3' ends of the cloned MMLV-RT gene.

The locations of the primers used for PCR amplification relative to the MMLV-RT containing vector are diagramed in FIG. 11. Primers A and B (having SEQ ID NO:14 and SEQ ID NO:15, respectively) were used to amplify a DNA fragment containing His-tag codons that were added to the 5' end of the cloned MMLV-RT gene to produce an MMLV-RT protein with an amino-terminal His-tag. Primers C and D (having SEQ ID NO:16 and SEQ ID NO:17, respectively) were used to amplify a DNA fragment containing His-tag codons that were added to the 3' end of the cloned MMLV-RT gene to produce an MMLV-RT protein with a carboxyl-terminal His-tag. The DNA fragments amplified using these primers were referred to by the designations "A/B" for the fragment amplified using primers A and B, and "C/D" for the fragment amplified using primers C and D; these designations were incorporated into the names of the plasmids resulting after cloning of the amplified fragments, as described below.

FIG. 12 shows the sequences of these primers with functional components indicated. Each primer contains a "spacer" sequence 5' to the endonuclease recognition sequence (Nco I in SEQ ID NO:14, Kpn I in SEQ ID NO:15, Bgl II in SEQ ID NO:16, and Hind III in SEQ ID NO:17). The 18 residues encoding the His tag are indicated by the sequence under the line labeled "6×his" in SEQ ID NOS:14 and 17. The start codon (ATG) and the codon encoding the amino-terminal Gly residue of MMLV-RT are also labeled under SEQ ID NO:14.

1. 5' His-Tagged MMLV-RT Construct

To incorporate a His tag consisting of six histidine residues into the amino-terminal region of the MMLV-RT protein, just downstream from the initial residue, primer "A" having SEQ ID NO:14 and primer "B" having SEQ ID NO:15 were synthesized and mixed with purified template DNA of pUC18N SD9D MMLV Gly under PCR amplification conditions to produce an amplified fragment of 301 bp. The 100 μl PCR reaction included: 10 mM each dNTP, 1 ng template DNA, 50 pmol of each primer, PCR buffer (10 mM KCl, 10 mM $(NH_4)_2SO_4$, 20 mM Tris-HCl (pH 8.75), 2 mM $MgSO_4$, 0.1% TRITON® X-100 and 0.1 mg/ml BSA) and thermostable DNA polymerase (cloned Pfu DNA polymerase, STRATAGENE®, La Jolla, Calif.), overlaid with 50–100 μl of oil. The PCR reaction was performed in a Perkin-Elmer Thermocyler programmed to incubate 4 min at 95° C, followed by 30 cycles each consisting of 1 min at 95° C., 1 min at 55° C. and 2 min at 72° C., and then cooling to 4° C.

Following PCR, the amplified 301 bp fragment was purified and digested with restriction endonucleases Nco I and Kpn I using standard methods (NEW ENGLAND BIO LABS Buffer I and Nco I, and BRL™ Kpn I). Following incubation with the restriction endonucleases, the digested DNA was electrophoretically separated on an agarose gel (50/% NUSIEVE™ agarose in TAE buffer) with standards for comparison (Hae III-digested phi-X 174 markers, uncut PCR amplified fragment and PCR amplified fragment cut with Kpn I or Nco I). The Nco I and Kpn I digested fragment of 287 bp was isolated from the gel and purified using phenol and chloroform extractions.

The vector clone, pUC18N SD9D MMLV Gly was linearized by digestion with Kpn I (for 2.25 hr at 37° C., to produce a 4646 bp DNA), followed by partial digestion with Nco I (for 5 min to 30 min at room temperature, taking aliquots at 5 min intervals). The digested vector clone DNA was then electrophoretically separated on a 0.9% agarose gel with molecular size standards (Hind III cut λ DNA and EcoR I, Hind III and BamH I cut λ DNA) for comparison. A 4380 bp fragment was isolated from the gel and purified using phenol and chloroform extractions, and ethanol precipitation.

The Nco I and Kpn I digested 287 bp fragment from the PCR amplified DNA was mixed with the 4380 bp fragment and the fragments were coprecipitated with 0.3 M sodium acetate and ethanol. The fragments were suspended in ligation buffer and ligated using T4 ligase using standard methods (overnight at 12° C.). The ligated DNA was transformed into *E. coli* Invαf' host cells using standard methods and colonies were selected for ampicillin resistance. Plasmid DNA was prepared from 1.5 ml of saturated culture of ampicillin-resistant cells using standard lysis and purification methods (QIAGEN® plasmid miniprep procedure) and the isolated DNA was sequenced using an automated dideoxy-sequencing method (thermocycle sequencing on a GENEAMP 9600 (Perkin Elmer Corp.), using a primer located 5' of the Nco I site (i.e., in the vector) and 25 cycles of 96° C. for 10 sec, 50° C. for 5 sec and 4 min, followed by separation and detection of fluorescent-labeled extension products using a 47 cm capillary at 50° C., using an ABI PRISM 310 Autosequencer (Perkin Elmer Corp.). Of 16 clones analyzed, two contained the 5' His tag sequence expected to result from insertion of the amplified fragment containing six histidine codons; other clones contained the parent clone sequence or contained a deletion from Nco I site at coordinate 1 to the Nco I site at coordinate 1784 of the parent clone. One of the two clones containing the 5' His tag sequence, designated plasmid pUC18N SD9D MMLV-RT A/B-His, was used for subsequent experiments.

A derivative of this plasmid was made that included insertion of the Tet gene substantially as described for the constructs illustrated in FIGS. 8 and 9. Plasmid pUC18N SD9D MMLV-RT A/B-His DNA was digested with restriction endonuclease Aat II and ligated with the Tet-containing Aat II fragment isolated from pUC Tet(+) (FIGS. 8E and 9D) as described above, using T4 DNA ligase. The ligated DNA was transformed into competent *E. coli* Invαf' cells using standard procedures and tetracycline-resistant colonies were selected on LB+Tet agar plates. Individual clones were grown, plasmid DNA purified from each and the DNA was digested with endonuclease BamH I to determine the orientation of the Tet-containing insertion in the plasmid. Plasmids with the tetracycline-resistance gene in the same orientation as the MMLV RT gene with respect to transcription were designated pUC18N SD9D MMLV-RT A/B-His Tet.

2. 3' His-Tagged MMLV-RT Construct

To incorporate a His tag consisting of six histidine residues into the carboxy-terminal region of the MMLV-RT protein, immediately upstream of the stop codon, primers having SEQ ID NO:16 and SEQ ID NO:17 were synthesized and mixed with purified template DNA of pUC18N SD9D MMLV Gly under PCR amplification conditions to produce an amplified fragment of 183 bp. The PCR reaction was performed substantially as described above except that the thermocyling incubations consisted of 5 min at 95° C., followed by 30 cycles each consisting of 1 min at 95° C., 30 sec at 55° C. and 1 min at 72° C., and then cooling to 4° C.

Following PCR, the amplified DNA was purified and digested sequentially with restriction endonucleases Bgl II and Hind III (2 hr at 37° C. for each) using standard methods and the digested DNA was electrophoretically separated on a 2% agarose gel substantially as described above, using molecular size standards for comparison. The Bgl II and Hind III digested fragment of 171 bp was isolated from the gel and purified using phenol and chloroform extractions and ethanol precipitation.

The vector clone, pUC18N SD9D MMLV Gly, was cut sequentially with Hind III and Bgl II (3 hr at 37° C. for each) to produce a digested vector clone DNA fragment of 4475 bp (i.e., without the fragment from the Bgl II site at position 1852 to the Hind III site at position 2023 of pUC18N SD9D MMLV Gly). The vector DNA fragment was electrophoretically separated on a 1% agarose gel, purified substantially as described above, and ligated with the Bgl II and Hind III digested PCR amplified DNA using T4 DNA ligase. The ligated DNA was transformed into *E. coli* Invαf' host cells using standard methods and colonies were selected for ampicillin resistance. Plasmid DNA was prepared from 1.5 ml of saturated culture of four clones using standard lysis and purification methods (QIAGEN® plasmid miniprep procedure) and the isolated DNA was sequenced using an automated sequencing method substantially as described above but using a primer located 3' of the Hind III site (i.e., in the vector). All four sequenced clones contained the expected sequence of the 3' His-tag insert expected to result from insertion of the amplified and endonuclease digested fragment containing the six histidine codons. The plasmid constructs were designated pUC18N SD9D MMLV-RT C/D-His.

EXAMPLE 12

Enzyme Activity of His-tagged Recombinant MMLV RT in Cell Lysates

To assay enzyme activity of both the 5' and 3' His-tagged constructs the, pUC18N SD9D MMLV-RT A/B-His clone and pUC18N SD9D MMLV-RT C/D-His clone were grown overnight in small cultures (2.5 ml LB containing 100 μg/ml ampicillin or "LB+Amp") and the RT activities of cell lysates were assayed using methods substantially as described in Example 1, except that the cell wash buffer contained 50 mM NaCl. RT activity was assayed substantially as described in Example 1 using duplicate samples for each lysate and a culture of the parental clone of pUC18N SD9D MMLV Gly in $E.$ $coli$ strain JM104 for comparison, as well as a stock solution of known activity to serve as a calibrator. In these tests, the non-His-tagged MMLV RT had 5.64 U/μl of lysate, the 5' His-tagged MMLV RT had 1.18 U/μl of lysate and the 3' His-tagged MMLV RT had 26.25 U/μl of lysate. Therefore, both forms of the His-tagged MMLV RT produced from the recombinant constructs described in Example 11 retained RT activity.

In another experiment, using cell lysates prepared using the same method and assayed for RT by the same method, a cell lysate prepared from a clone containing the pUC18N SD9D MMLV-RT A/B-His Tet plasmid was also included. In this experiment, the 5' His-tagged MMLV RT from the Tet-containing construct had 14.35 U/μl of lysate, the 5' His-tagged MMLV RT from construct without the Tet gene had 25.06 U/μl of lysate and the 3' His-tagged MMLV RT had 10.50 U/μl of lysate. Although the RT activities detected from different cell lysates varied somewhat, both the amino-terminal His-tagged and carboxyl-terminal His-tagged RT showed significant RT activity even in unpurified cell lysates.

EXAMPLE 13

Purification of 5' His-tagged and 3' His-tagged Recombinant MMLV RT Proteins Using Metal Affinity Chromatography For purification of the His-tagged MMLV RT protein using immobilized metal affinity chromatography, 100 ml cultures of $E.$ $coli$ strain Invαf cells containing the pUC18N SD9D MMLV-RT C/D-His plasmid or the pUC18N SD9D MMLV-RT A/B-His plasmid (in LB+Amp) or the pUC18N SD9D MMLV-RT A/B-His Tet plasmid (in LB+Tet) were grown overnight at 37° C. Cell lysates were prepared by pelleting the cells by centrifugation (10–15 min, 6000 rpm in a GSA rotor), aspirating and discarding the supernatant, washing the cells with 5 ml of wash buffer (50 mM Tris-HCL, pH 8.0, 50 mM NaCl, 5 mM EDTA, 0.25 M sucrose, allowing 5 min at room temperature for the cells to equilabrate), pelleting the cells as described above, aspirating and discarding the supernatant and then freezing the cell pellet (dry ice or −70° C.). Then, cells were thawed for 15 min and suspended in 1 ml of lysis buffer (0.01 M imidazole, 0.3 M NaCl in 1×NaH$_2$PO$_4$ buffer, pH 8.0), and then adding about 1.5 mg of lysozyme and mixing, followed by incubation on ice for 30 min. The cells were then homogenized on ice using standard methods (in a WHEATON™ 7 ml homogenizer or a 2 ml KONTES™ homogenizer) and the lysate was centrifuged (15,000 rpm in a microcentrifuge for 30 min) to pellet debris leaving the supernatant cell lysate for further purification.

A nickel-nitrilotriacetic acid resin (Ni-NTA) in a column (QIAEXPRESS® System, QIAGEN®, Venlo, The Netherlands) was equilibrated with lysis buffer and then 600 μl of supernatant cell lysate was loaded onto the column and the flow-through volume was collected. The Ni-NTA resin was washed twice with 600 μl of column wash buffer (0.02 M imidazole, 0.3 M NaCl in 1×NaH$_2$PO$_4$ buffer, pH 8.0). Protein was eluted from the resin using two 100 μl portions of elution buffer (0.26 M imidazole, 0.3 M NaCl in 1×NaH$_2$PO$_4$ buffer, pH 8.0); 2 mM PMSF was added to the collected fractions of purified protein, which were stored at −20° C. until assayed for RT activity.

RT activity was assayed substantially as described in Examples 1 and 12, and the units of activity were calculated for each of the different sources of chromatographically purified proteins. In these assays, the 5' His-tagged MMLV RT from the Tet-containing construct had 14.79 U/μl of eluate, the 5' His-tagged MMLV RT from construct without the Tet gene had 8.60 U/μl of eluate and the 3' His-tagged MMLV RT had 36.01 U/μl of eluate.

In a separate experiment, a lysate was made from a 250 ml culture of the pUC18N SD9D MMLV-RT A/B-His Tet clone by increasing the volume of lysis buffer to 2.5 ml and the lysozyme to about 4 mg and dividing the lysate between five Ni-NTA columns for purification. The proteins were eluted from the Ni-NTA columns using two 200 μl portions of elution buffer for each column. Following elution, the eluates were pooled to produce about 2.0 μl which was dialyzed for about 1 hr at 4° C. to concentrate the proteins using standard methods (using a PIERCE SLIDE-A-LYZER™ with a 10,000 molecular weight cut off and, PIERCE SIDE-A-LYZER Concentrating solution). The volume of eluate was reduced to about 650 μl following dialysis and then equilibrated for storage using a solution of 50% glycerol, 20 mM, TRIS-HCL, pH 7.4, 0.1 mM EDTA, 100 mM NaCl, 1 mM DTT and 0.01% TRITON® X-100.

In another experiment, the starting culture was 500 ml of the pUC18N SD9D MMLV-RT A/B-His clone and the eluted protein was reduced from about 2.0 ml to about 250 μl by dialysis against a concentrating solution for about 1.5 hr. Protein purity was checked visually by gel electrophoresis (see Example 14).

EXAMPLE 14

SDS-Polyacrylamide Gel Electrophoresis Analysis of Protein in Cell Lysates and Purified by Using Metal Affinity Chromatography To visually determine if the affinity chromatography described in Example 13 had removed contaminating proteins present in cell lysates, a portion of the eluates described in Example 13 were separated using SDS-polyacrylamide gel electrophoresis (Laemmli U. K., 1970, $Nature$ 227:680), substantially as described in Example 5 except that a 10%

Bis-Tris, NUPAGE™ gel was used (Novex, San Diego, Calif.). For comparison, lysates of cells containing the clones were prepared and electrophoretically separated under identical conditions.

For preparation of the cell lysates, 0.5 ml of overnight cell cultures for each of the clones (pUC18N SD9D MMLV Gly in *E. coli* strain JM104; pUC18N SD9D MMLV-RT C/D-His, or pUC18N SD9D MMLV-RT A/B-His, or pUC18N SD9D MMLV-RT A/B-His Tet in *E. coli* strain Invαf) and *E. coli* cells without any plasmid were pelleted by centrifugation. The supernatant was removed and the cell pellets were suspended in SDS gel loading buffer containing 2.5% β-mercatoethanol and boiled for 5 min before cooling on ice. From each cell lysate, 20 µl was applied to a gel lane.

For the eluates obtained from Ni-NTA columns, 20 µl of eluate was added to 100 µl of SDS gel loading buffer containing 2.5% β-mercatoethanol and treated as described above. For each eluate, 40 µl of the mixture was applied to a gel lane.

Molecular weight standards were electrophoretically separated on the same gel as the samples and electrophoretic separation was completed in 45 min. Following electrophoresis, the gels were soaked in a denaturing fixative, a methanol-containing staining solution, and in water to remove background gel staining, using standard methods. Stained gels were preserved by drying on a paper backing.

In all of the gel lanes containing cell lysates, the proteins produced a large amount of stained material ranging from greater than 100 kD to less than 14.4 kD. By comparison with the *E. coli* cell lysate that did not contain a plasmid bearing an MMLV-RT gene, the lysates for clones of the MMLV-RT, with or without a His-tag, all produced a visible band having an apparent molecular weight in the size range of mature native MMLV-RT (about 70 kD) that was not present in the control lysate. In the gel lanes containing the metal ion affinity chromatography eluates, the amount of background protein was significantly reduced (about 10 discrete bands were visible) and the band of about 70 kD was the most prominent staining band visible. The eluates produced from the clones containing pUC18N SD9D MMLV-RT C/D-His and pUC18N SD9D MMLV-RT A/B-His Tet contained the greatest amounts of the band of about 70 kD. The eluate from the pUC18N SD9D MMLV-RT A/B-His Tet clone also contained a predominant band of about 58 kD.

When a similar aliquot of the concentrated protein eluate described in Example 13, obtained from pUC18N SD9D MMLV-RT A/B-His Tet clone, was electrophoretically separated and visualized by staining, a similar pattern of bands was seen. That is, the larger scale preparation technique and concentration of the eluate produced a protein pattern in which a band of about 70 kD was the most prominent staining band, a band of about 58 kD was also prominent and the other visible bands (about 10 or fewer) were visible throughout the rest of the gel (between about 116 kD to 14.4 kD molecular weight range). For the proteins purified from 500 ml of the pUC18N SD9D MMLV-RT A/B-His clone (described in Example 13), the proteins visualized were similar to those seen with the smaller scale preparations of the same protein. Thus, the scaled-up lysate preparation and concentration of eluate following elution from the metal ion column did not significantly change the material recovered.

EXAMPLE 15

Protein Concentration and Enzyme Activity in Eluate Purified by Using Metal Affinity Chromatography The purified and concentrated protein produced from the 500 ml culture of the pUC18N SD9D MMLV-RT A/B-His clone described in Example 13 was assayed for protein concentration using routine absorbance methods relative to a known standard, and reverse transcriptase polymerase activity in the purified protein was determined. The purified protein obtained from the pUC18N SD9D MMLV-RT A/B-His clone was at a concentration of 0.698 µg/µl.

The RNA-directed DNA polymerase activity of the purified protein was then assayed using a well-known primer extension procedure in which incorporation of $^3$H-dTTP into DNA was measured by comparison with activity of a known RT enzyme that was assayed in parallel reactions. Briefly, the enzymes were sequentially diluted and portions of each dilution were then incubated for 20 min at 37° C. in a reaction mixture that contained template RNA, a complementary DNA oligonucleotide primer and unlabeled dNTPs in addition to $^3$H-dTTP in salt conditions to support polymerase activity. After incubation, the reactions were terminated by adding EDTA to a final concentration of 50 mM. Then a portion of each reaction was spotted onto a filter (DE81 filters) and dried for at least 30 min. Then, the filters washed three times with 2×SSC for 5 min for each wash, rinsed twice with 95% ethanol and dried for about 1. hr. The radioactivity present on each of the dried filters was determined as cpm using standard liquid scintillation measurement. A standard curve was generated for the known enzyme by plotting the detected cpm relative to the known units of RT polymerase activity ("RTU"). The RTU present in the diluted purified protein obtained from the pUC18N SD9D MMLV-RT A/B-His clone was then calculated by comparing the detected cpm of the purified protein dilutions against the standard curve. Based on these assays, the standard RT protein had a specific activity of 1071 RTU/mg, and the protein purified from the the pUC18N SD9D MMLV-RT A/B-His clone had a specific activity of 275 RTU/mg. Thus, the purified His-tagged protein exhibited polymerase activity. Although the specific activity demonstrated in this example was not as great as demonstrated for the standard RT protein, the relative ease of purifying the His-tagged protein makes it useful for a number of applications in which rapid purification is important.

These nonlimiting examples demonstrate some embodiments of the present invention which is defined by the claims that follow.

We claim:

1. A recombinant DNA molecule comprising:
   (1) a DNA fragment comprising a nucleic acid which encodes a single-chain recombinant polypeptide having RNA-directed and DNA-directed DNA polymerase activities and RNase H activity,
      wherein the nucleic acid comprises a coding sequence, CTGAACATC, that occurs within 30 nucleotides of a start codon, ATG, of the sequence encoding the recombinant polypeptide, as shown in SEQ ID NO:3 or SEQ ID NO:14,
      wherein the nucleic acid comprises the sequence of SEQ ID NO:19 which comprises from nucleotides 2617 to 4569 of a Moloney murine leukemia virus (MMLV) genomic sequence,
      wherein the nucleic acid comprises the DNA sequence shown in SEQ ID NO:14 or SEQ ID NO:17 encoding a plurality of contiguous histidine residues located at or near an amino-terminus or carboxy-terminus of the recombinant polypeptide,
      and wherein the nucleic acid comprises a stop codon adjacent to the 3' end of sequence encoding the recombinant polypeptide;
   (2) a DNA fragment comprising a promoter sequence for expressing the nucleic acid which encodes the recombinant polypeptide in an *E. coli* host cell;
   (3) a DNA fragment comprising a ribosome binding site containing the sequence TAAGGAGGT complementary to *E. coli* 16S rRNA and a spacer region consisting of the sequence TTAAAAACC separating the ribosome binding site from the start codon in the nucleic acid which encodes the recombinant polypeptide, and
   (4) a DNA fragment containing an origin of replication that promotes autonomous replication of a vector in an *E. coli* host cell,
   wherein the DNA fragments are operably linked so that the fragments are replicated together in the *E. coli* host cell and the nucleic acid which encodes the recombinant polypeptide is expressed in the *E. coli* host cell to produce a single chain recombinant polypeptide having a reverse transcriptase activity.

2. The recombinant DNA molecule of claim 1, wherein the DNA sequence encoding the plurality of contiguous histidine residues encodes six histidine residues.

3. The recombinant DNA molecule of claim 1, wherein the nucleic acid which encodes the single chain recombinant polypeptide with the plurality of contiguous histidine residues located at or near the amino-terminus is SEQ ID NO:21.

4. The recombinant DNA molecule of claim 1, wherein the nucleic acid which encodes the single chain recombinant polypeptide with the plurality of contiguous histidine residues located at the carboxy-terminus is SEQ ID NO:20.

5. A method for producing a recombinant polypeptide having RNA-directed and DNA-directed DNA polymerase activities comprising the steps:
   (1) providing a plasmid comprising
      (A) a recombinant DNA sequence encoding a single-chain recombinant polypeptide having reverse transcriptase activity,
         wherein the recombinant DNA sequence comprises a coding sequence, CTGAACATC, that occurs within 30 nucleotides of a start codon, ATG, of the sequence encoding the recombinant polypeptide, as shown in SEQ ID NO:3 or SEQ ID NO:14,
         wherein the recombinant DNA sequence comprises from nucleotides 2617 to 4569 of MMLV genomic sequence, as shown in SEQ ID NO:19,
         wherein the recombinant DNA sequence comprises a sequence encoding a plurality of contiguous histidine residues located at or near an amino-terminus or carboxy-terminus of the recombinant polypeptide, as shown in SEQ ID NO:14 or SEQ ID NO:17,
         and wherein the recombinant DNA sequence comprises a stop codon adjacent to the 3' end of sequence encoding the recombinant polypeptide,
      (B) at least one selectable marker gene,
      (C) a promoter sequence for expression of the recombinant DNA sequence in an *E. coli* host cell,
      (D) a ribosome binding site containing the sequence TAAGGAGGT complementary to *E. coli* 16S rRNA,
      (E) a spacer region consisting of the sequence TTAAAAACC separating the ribosome binding site from the start codon in the recombinant DNA sequence encoding the recombinant polypeptide, and
      (F) an origin of replication for autonomous replication of the plasmid within an *E. coli* host cell;
   (2) growing *E. coli* host cells containing the plasmid in a liquid culture that promotes cell division and expression of the recombinant DNA sequence;
   (3) lysing the *E. coli* host cells to form a cell lysate; and
   (4) purifying the recombinant polypeptide encoded by the recombinant DNA sequence from the cell lysate using metal ion affinity chromatography, thereby producing a purified recombinant polypeptide having reverse transcriptase activity.

6. The method of claim 5, wherein the metal ion affinity chromatography is performed using nickel ions attached to a resin to retain the recombinant polypeptide having reverse transcriptase activity.

7. The method of claim 6, wherein the recombinant polypeptide having reverse transcriptase activity is eluted from the nickel ions attached to the resin using an imidazole-containing buffer.

8. The method of claim 5, wherein the recombinant polypeptide purified using metal ion affinity chromatography has an apparent molecular weight of about 70,000 daltons, and wherein residues 1 to 11 of the recombinant polypeptide are encoded by nucleotides 9 to 41 of SEQ ID NO:14.

9. The method of claim 5, wherein the purifying step produces a recombinant polypeptide having RNA-directed DNA polymerase activity having a specific activity of at least 275 U/mg total protein as determined using a primer extension reaction and by comparison to RNA-directed DNA polymerase activity of a known reverse transcriptase enzyme.

10. The recombinant DNA molecule of claim 1, wherein the nucleic acid encoding the single chain recombinant polypeptide having a reverse transcriptase activity comprises nucleotides 9 to 41 of SEQ ID NO:14.

* * * * *

UNITED STATES PATENT AND TRADEMARK OFFICE
CERTIFICATE OF CORRECTION

PATENT NO.      : 6,593,120 B1
DATED           : July 15, 2003
INVENTOR(S)     : Riggs et al.

It is certified that error appears in the above-identified patent and that said Letters Patent is hereby corrected as shown below:

<u>Column 9,</u>
Line 53, insert -- (SEQ ID NO:18) -- after "bases".

<u>Column 14,</u>
Line 48, delete ")" after "copolymer".

<u>Column 15,</u>
Line 40, delete the word "space".

<u>Column 18,</u>
Line 31, delete "NON" and insert in its place -- NONIDET --.
Line 32, insert -- ) -- after "(Octylphenoxy)-Polyethoxyethanol".
Line 33, delete ")" after "glycerol".
Lines 49-50, delete "(2,2'-dipyridyldisulfido, 2,2'dipyridylpyridne" and insert in its place -- (2,2'dipyridyl disulfide, 2,2'-dithiodipyridine) --.
Line 50, insert -- Aldrich -- before "Chemical Company".

<u>Column 27,</u>
Line 66, delete "HCL" and insert in its place -- HCl --.

<u>Column 28,</u>
Line 48, delete "TRIS-HCL" and insert in its place -- Tris-HCl --.

Signed and Sealed this

Thirteenth Day of January, 2004

JON W. DUDAS
*Acting Director of the United States Patent and Trademark Office*

SEQUENCE LISTING

<160> NUMBER OF SEQ ID NOS: 21

<210> SEQ ID NO 1
<211> LENGTH: 114
<212> TYPE: DNA
<213> ORGANISM: Artificial Sequence
<220> FEATURE:
<223> OTHER INFORMATION: Description of Artificial Sequence:
      Oligonucleotide used to construct plasmid pUC 18N

<400> SEQUENCE: 1
ggcatgcagc tggcacgaca ggtttcccga ctggaaagcg ggcagtgagc gcaacgcaat      60
taatgtgagt tagctcactc attaggcacc ccaggcttta cactttatgc ttcc           114

<210> SEQ ID NO 2
<211> LENGTH: 111
<212> TYPE: DNA
<213> ORGANISM: Artificial Sequence
<220> FEATURE:
<223> OTHER INFORMATION: Description of Artificial Sequence:
      Oligonucleotide used to construct plasmid pUC 18N

<400> SEQUENCE: 2
aagctcgaat tcgtaatcat ggccatggct gtttcctgtg tgaaagtttt atccgctcac      60
aattccacac aacatacgag ccggaagcat aaagtgtaaa gcctgggtgc c              111

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide used to construct 5' portion of RT
      gene coding for glycine at amino acid 2 position

<400> SEQUENCE: 3
catgggtctg aacatcgaag atga                                             24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide used to construct 5' portion of RT
      gene coding for glycine at amino acid 2 position

<400> SEQUENCE: 4
tcatcttcga tgttcagacc                                                  20

<210> SEQ ID NO 5
<211> LENGTH: 115
<212> TYPE: DNA
<213> ORGANISM: Artificial Sequence
<220> FEATURE:
<223> OTHER INFORMATION: Description of Artificial Sequence:
      Oligonucleotide used to modify ribosome binding
      site and spacer region

<400> SEQUENCE: 5
gagctcgaat tcgtaatcat ggccatggtt taaacctcct tagtgaaatt gttatccgct      60
cacaattcca cacaacatac gagccggaag cataaagtgt aaagcctggg gtgcc          115

```
<210> SEQ ID NO 6
<211> LENGTH: 116
<212> TYPE: DNA
<213> ORGANISM: Artificial Sequence
<220> FEATURE:
<223> OTHER INFORMATION: Description of Artificial Sequence:
      Oligonucleotide used to modify ribosome binding
      site and spacer region

<400> SEQUENCE: 6
gagctcgaat tcgtaatcat ggccatggtw ttaaacctcc ttagtgaaat tgttatccgc      60
tcacaattcc acacaacata cgagccggaa gcataaagtg taaagcctgg ggtgcc        116

<210> SEQ ID NO 7
<211> LENGTH: 117
<212> TYPE: DNA
<213> ORGANISM: Artificial Sequence
<220> FEATURE:
<223> OTHER INFORMATION: Description of Artificial Sequence:
      Oligonucleotide used to modify ribosome binding
      site and spacer region

<400> SEQUENCE: 7
gagctcgaat tcgtaatcat ggccatggtw wttaaacctc cttagtgaaa ttgttatccg      60
ctcacaattc cacacaacat acgagccgga agcataaagt gtaaagcctg ggtgcc        117

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer for
      cDNA synthesis

<400> SEQUENCE: 8
taccttgtta cgacttcacc cca                                              23

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Primer for
      cDNA synthesis

<400> SEQUENCE: 9
cttagatgct ttcagc                                                      16

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide used to construct pUC18 MMLV
      Tailed

<400> SEQUENCE: 10
aggcagccat cacagagact ccagacacct ctaccctcct ctaata                     46

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide used to construct pUC18 MMLV
```

Tailed

<400> SEQUENCE: 11
agcttattag aggagggtag aggtgtctgg agtctctgtg atggctgcct ttc        53

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: 5'codons of
      MMLV-RT gene preferred by E. coli

<400> SEQUENCE: 12
atgggtctga acatc        15

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:  Ribosome
      binding site, spacer sequence and initiation codon

<400> SEQUENCE: 13
taaggaggtt taaaaaacc        19

<210> SEQ ID NO 14
<211> LENGTH: 57
<212> TYPE: DNA
<213> ORGANISM: Artificial Sequence
<220> FEATURE:
<223> OTHER INFORMATION: Description of Artificial Sequence: Primer used
      to introduce His-tag codons at 5' end of MMLV-RT gene

<400> SEQUENCE: 14
gctgctccat gggtcaccat caccatcacc atctgaacat cgaagatgag catcggc        57

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer used
      to introduce His-tag codons at 5' end of MMLV-RT gene

<400> SEQUENCE: 15
cgtcgtggta ccagtattcc ctggtccaac        30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Primer used
      to introduce His-tag codons at 3' end of MMLV-RT gene

<400> SEQUENCE: 16
catcatagat cttggcccta ctaaaagccc        30

<210> SEQ ID NO 17
<211> LENGTH: 58
<212> TYPE: DNA
<213> ORGANISM: Artificial Sequence
<220> FEATURE:
<223> OTHER INFORMATION: Description of Artificial Sequence: Primer used
      to introduce His-tag codons at 3' end of MMLV-RT gene

<400> SEQUENCE: 17
caacaaaagc ttagtgatgg tgatggtgat ggaggagggt agaggtgtct ggagtctc       58

<210> SEQ ID NO 18
<211> LENGTH: 2336
<212> TYPE: DNA
<213> ORGANISM: Moloney murine sarcoma virus

<400> SEQUENCE: 18
caggttatgg gaccaatggg gcagcccctg caagtgttga ccctaaatat agaagatgag      60
catcggctac atgagacctc aaaagagcca gatgtttctc tagggtccac atggctgtct    120
gattttcctc aggcctgggc ggaaaccggg gcatggggac tggcagttcg ccaagctcct    180
ctgatcatac tctgaaagc aacctctacc cccgtgtcca taaacaata ccccatgtca      240
caagaagcca gactggggat caagcccac atacagagac tgttggacca gggaatactg     300
gtaccctgcc agtccccctg gaacacgccc ctgctacccg ttaagaaacc agggactaat    360
gattataggc ctgtccagga tctgagagaa gtcaacaagc gggtggaaga catccacccc    420
accgtgccca acccttacaa cctcttgagc gggctcccac cgtcccacca gtggtacact    480
gtgcttgatt taaggatgc cttttctgc ctgagactcc accccaccag tcagcctctc       540
ttcgcctttg agtggagaga tccagagatg gaatctcag acaattgac ctggaccaga      600
ctcccacagg gtttcaaaaa cagtcccacc ctgtttgatg aggcactgca cagagaccta    660
gcagacttcc ggatccagca cccagacttg atcctgctac agtacgtgga tgacttactg    720
ctggccgcca cttctgagct agactgccaa caaggtactc gggccctgtt acaaacccta    780
gggaacctcg ggtatcgggc ctcggccaag aaagcccaaa tttgccagaa acaggtcaag    840
tatctggggt atcttctaaa agagggtcag agatggctga ctgaggccag aaaagagact    900
gtgatggggc agcctactcc gaagacccct cgacaactaa gggagttcct agggacggca    960
ggcttctgtc gcctctggat ccctgggttt gcagaaatgg cagcccccctt gtaccctctc   1020
accaaaacgg ggactctgtt taattgggc ccagaccaac aaaaggccta tcaagaaatc    1080
aagcaagctc ttctaactgc cccagccctg gggttgccag atttgactaa gcccttttgaa  1140
ctctttgtcg acgagaagca gggctacgcc aaaggtgtcc taacgcaaaa actgggacct   1200
tggcgtcggc cggtggccta cctgtccaaa aagctagacc cagtagcagc tgggtggccc   1260
ccttgcctac ggatggtagc agccattgcc gtactgacaa aggatgcagg caagctaacc   1320
atgggacagc cactagtcat tctggcccc catgcagtag aggcactagt caaacaaccc   1380
cccgaccgct ggcttttccaa cgcccggatg actcactatc aggccttgct tttggacacg   1440
gaccgggtcc agttcggacc ggtggtagcc ctgaaccccgg ctacgctgct cccactgcct   1500
gaggaagggc tgcaacacaa ctgccttgat atcctggccg aagcccacgg aacccgaccc    1560
gacctaacgg accagccgct cccagacgcc gaccacacct ggtacacgga tggaagcagt    1620
ctcttacaag agggacagcg taaggcggga gctgcggtga ccaccgagac cgaggtaatc    1680
tgggctaaag ccctgccagc cgggacatcc gctcagcggg ctgaactgat agcactcacc    1740
caggccctaa agatggcaga aggtaagaag ctaaatgttt atactgatag ccgttatgct    1800
tttgctactg cccatatcca tggagaaata tacagaaggc gtgggttgct cacatcagaa    1860
ggcaaagaga tcaaaaataa agacgagatc ttggcccta caaaagccct ctttctgccc    1920
aaaagactta gcataatcca ttgtccagga catcaaaagg acacagcgc cgaggctaga    1980

| | |
|---|---|
| ggcaaccgga tggctgacca agcggcccga aaggcagcca tcacagagac tccagacacc | 2040 |
| tctaccctcc tcatagaaaa ttcatcaccc tacacctcag aacattttca ttacacagtg | 2100 |
| actgatataa aggacctaac caagttgggg gccatttatg ataaaacaaa gaagtattgg | 2160 |
| gtctaccaag gaaaacctgt gatgcctgac cagtttactt ttgaattatt agactttctt | 2220 |
| catcagctga ctcacctcag cttctcaaaa atgaaggctc tcctagagag aagccacagt | 2280 |
| ccctactaca tgctgaaccg ggatcgaaca ctcaaaaata tcactgagac ctgcaa | 2336 |

<210> SEQ ID NO 19
<211> LENGTH: 1953
<212> TYPE: DNA
<213> ORGANISM: Moloney murine sarcoma virus

<400> SEQUENCE: 19

| | |
|---|---|
| agcatcggct acatgagacc tcaaaagagc cagatgtttc tctagggtcc acatggctgt | 60 |
| ctgattttcc tcaggcctgg gcggaaaccg ggggcatggg actggcagtt cgccaagctc | 120 |
| ctctgatcat acctctgaaa gcaacctcta ccccgtgtc cataaaacaa taccccatgt | 180 |
| cacaagaagc cagactgggg atcaagcccc acatacagag actgttggac cagggaatac | 240 |
| tggtaccctg ccagtccccc tggaacacgc ccctgctacc cgttaagaaa ccagggacta | 300 |
| atgattatag gcctgtccag gatctgagag aagtcaacaa gcgggtggaa gacatccacc | 360 |
| ccaccgtgcc caaccttac aacctcttga gcgggctccc accgtcccac cagtggtaca | 420 |
| ctgtgcttga tttaaaggat gccttttcct gcctgagact ccaccccacc agtcagcctc | 480 |
| tcttcgccttt tgagtggaga gatccagaga tgggaatctc aggacaattg acctggacca | 540 |
| gactcccaca gggtttcaaa aacagtccca ccctgtttga tgaggcactg cacagagacc | 600 |
| tagcagactt ccggatccag cacccagact tgatcctgct acagtacgtg gatgacttac | 660 |
| tgctggccgc cacttctgag ctagactgcc aacaaggtac tcgggccctg ttacaaaccc | 720 |
| tagggaacct cgggtatcgg gcctcggcca agaaagccca aatttgccag aaacaggtca | 780 |
| agtatctggg gtatcttcta aaagagggtc agagatggct gactgaggcc agaaaagaga | 840 |
| ctgtgatggg gcagcctact ccgaagaccc ctcgacaact aagggagttc ctagggacgg | 900 |
| caggcttctg tcgcctctgg atccctgggt ttgcagaaat ggcagccccc ttgtaccctc | 960 |
| tcaccaaaac ggggactctg tttaattggg gcccagacca acaaaaggcc tatcaagaaa | 1020 |
| tcaagcaagc tcttctaact gccccagccc tggggttgcc agatttgact aagcccttg | 1080 |
| aactctttgt cgacgagaag cagggctacg ccaaggtgt cctaacgcaa aaactgggac | 1140 |
| cttggcgtcg gccggtggcc tacctgtcca aaaagctaga cccagtagca gctgggtggc | 1200 |
| cccttgcct acgatggta gcagccattg ccgtactgac aaaggatgca ggcaagctaa | 1260 |
| ccatgggaca gccactagtc attctggccc ccatgcagt agaggcacta gtcaaacaac | 1320 |
| cccccgaccg ctggctttcc aacgcccgga tgactcacta tcaggccttg cttttggaca | 1380 |
| cggaccgggt ccagttcgga ccggtggtag ccctgaaccc ggctacgctg ctcccactgc | 1440 |
| ctgaggaagg gctgcaacac aactgccttg atatcctggc cgaagcccac ggaacccgac | 1500 |
| ccgacctaac ggaccagccg ctcccagacg ccgaccacac ctggtacacg gatggaagca | 1560 |
| gtctcttaca agagggacag cgtaaggcgg gagctgcggt gaccaccgag accgaggtaa | 1620 |
| tctgggctaa agccctgcca gccgggacat ccgctcagcg gctgaactg atagcactca | 1680 |
| cccaggccct aaagatggca gaaggtaaga agctaaatgt ttatactgat agccgttatg | 1740 |
| cttttgctac tgcccatatc catggagaaa tatacagaag gcgtgggttg ctcacatcag | 1800 |

-continued

```
aaggcaaaga gatcaaaaat aaagacgaga tcttggccct actaaaagcc ctctttctgc      1860
ccaaaagact tagcataatc cattgtccag gacatcaaaa gggacacagc gccgaggcta      1920
gaggcaaccg gatggctgac caagcggccc gaa                                   1953

<210> SEQ ID NO 20
<211> LENGTH: 2037
<212> TYPE: DNA
<213> ORGANISM: Artificial Sequence
<220> FEATURE:
<223> OTHER INFORMATION: Decription of Artificial Sequence: Recombinant
      reverse transcriptase gene

<400> SEQUENCE: 20
atgggtctga acatcgaaga tgagcatcgg ctacatgaga cctcaaaaga gccagatgtt        60
tctctagggt ccacatggct gtctgatttt cctcaggcct gggcggaaac cgggggcatg       120
ggactggcag ttcgccaagc tcctctgatc atacctctga agcaacctc taccccgtg        180 tccataaaac aataccccat gtcacaagaa gccagactgg ggatcaagcc ccacatacag       240
agactgttgg accagggaat actggtaccc tgccagtccc cctggaacac gcccctgcta       300
cccgttaaga aaccagggac taatgattat aggcctgtcc aggatctgag agaagtcaac       360
aagcgggtgg aagacatcca ccccaccgtg cccaacccctt acaacctctt gagcgggctc       420
ccaccgtccc accagtggta cactgtgctt gatttaaagg atgcctttt ctgcctgaga       480 ctccacccca ccagtcagcc tctcttcgcc tttgagtgga gagatccaga gatgggaatc       540
tcaggacaat tgacctggac cagactccca cagggtttca aaacagtcc caccctgttt       600 gatgaggcac tgcacagaga cctagcagac ttccggatcc agcacccaga cttgatcctg       660
ctacagtacg tggatgactt actgctggcc gccacttctg agctagactg ccaacaaggt       720
actcgggccc tgttacaaac cctagggaac ctcgggtatc gggcctcggc caagaaagcc       780
caaatttgcc agaaacaggt caagtatctg gggtatcttc taaaagaggg tcagagatgg       840
ctgactgagg ccagaaaaga gactgtgatg gggcagccta ctccgaagac ccctcgacaa       900
ctaagggagt tcctagggac ggcaggcttc tgtcgcctct ggatccctgg gtttgcagaa       960
atggcagccc ccttgtaccc tctcaccaaa acggggactg tgtttaattg gggcccagac      1020
caacaaaagg cctatcaaga aatcaagcaa gctcttctaa ctgccccagc cctggggttg      1080
ccagatttga ctaagccctt tgaactcttt gtcgacgaga agcagggcta cgccaaaggt      1140
gtcctaacgc aaaaactggg accttggcgt cggccggtgg cctacctgtc caaaaagcta      1200
gacccagtag cagctgggtg gccccttgc ctacggatgg tagcagccat tgccgtactg      1260
acaaaggatg caggcaagct aaccatggga cagccactag tcattctggc cccccatgca      1320
gtagaggcac tagtcaaaca acccccgac cgctggcttt ccaacgcccg gatgactcac      1380
tatcaggcct tgcttttgga cacggaccgg gtccagttcg gaccggtggt agccctgaac      1440
ccggctacgc tgctcccact gcctgaggaa gggctgcaac acaactgcct tgatatcctg      1500
gccgaagccc acggaacccg acccgaccta acggaccagc cgctcccaga cgccgaccac      1560
acctggtaca cggatggaag cagtctctta caagagggac agcgtaaggc gggagctgcg      1620
gtgaccaccg agaccgaggt aatctgggct aaagccctgc cagccgggac atccgctcag      1680
cgggctgaac tgatagcact cacccaggcc ctaaagatgg cagaaggtaa gaagctaaat      1740
gtttatactg atagccgtta tgcttttgct actgcccata tccatggaga aatatacaga      1800
aggcgtgggt tgctcacatc agaaggcaaa gagatcaaaa ataaagacga gatcttggcc      1860
```

```
ctactaaaag ccctctttct gcccaaaaga cttagcataa tccattgtcc aggacatcaa    1920
aagggacaca gcgccgaggc tagaggcaac cggatggctg accaagcggc ccgaaaggca    1980
gccatcacag agactccaga cacctctacc ctcctccatc accatcacca tcactaa       2037
```

<210> SEQ ID NO 21
<211> LENGTH: 2037
<212> TYPE: DNA
<213> ORGANISM: Artificial Sequence
<220> FEATURE:
<223> OTHER INFORMATION: Description of Artificial Sequence: Recombinant
      reverse transcriptase gene

<400> SEQUENCE: 21

```
atgggtcacc atcaccatca ccatctgaac atcgaagatg agcatcggct acatgagacc     60
tcaaaagagc cagatgtttc tctagggtcc acatggctgt ctgattttcc tcaggcctgg    120
gcggaaaccg ggggcatggg actggcagtt cgccaagctc tctgatcat acctctgaaa     180 gcaacctcta cccccgtgtc cataaaacaa taccccatgt cacaagaagc cagactgggg    240
atcaagcccc acatacagag actgttggac cagggaatac tggtaccctg ccagtccccc    300
tggaacacgc ccctgctacc cgttaagaaa ccagggacta atgattatag gcctgtccag    360
gatctgagag aagtcaacaa gcgggtggaa gacatccacc ccaccgtgcc caacccttac    420
aacctcttga gcggctccc accgtccac cagtggtaca ctgtgcttga tttaaaggat      480 gccttttttct gcctgagact ccaccccacc agtcagcctc tcttcgcctt tgagtggaga   540
gatccagaga tgggaatctc aggacaattg acctggacca gactcccaca gggtttcaaa   600
aacagtccca ccctgtttga tgaggcactg cacagagacc tagcagactt ccggatccag    660
cacccagact tgatcctgct acagtacgtg gatgacttac tgctggccgc cacttctgag    720
ctagactgcc aacaaggtac tcgggccctg ttacaaaccc tagggaacct cgggtatcgg    780
gcctcggcca agaaagccca aatttgccag aaacaggtca agtatctggg gtatcttcta    840
aaagagggtc agagatggct gactgaggcc agaaaagaga ctgtgatggg gcagcctact    900
ccgaagaccc ctcgacaact aagggagttc ctagggacgg caggcttctg tcgcctctgg    960
atccctgggt tgcagaaat ggcagccccc ttgtaccctc tcaccaaaac ggggactctg    1020
tttaattggg gccagacca acaaaaggcc tatcaagaaa tcaagcaagc tcttctaact   1080
gccccagccc tgggttgcc agatttgact aagccctttg aactctttgt cgacgagaag   1140
cagggctacg ccaaaggtgt cctaacgcaa aaactgggac cttggcgtcg gccggtggcc   1200
tacctgtcca aaaagctaga cccagtagca gctgggtggc cccttgcct acggatggta    1260 gcagccattg ccgtactgac aaaggatgca ggcaagctaa ccatgggaca gccactagtc    1320
attctggccc ccatgcagt agaggcacta gtcaaacaac ccccgaccg ctggctttcc     1380 aacgcccgga tgactcacta tcaggccttg cttttggaca cggaccgggt ccagttcgga   1440
ccggtggtag ccctgaaccc ggctacgctg ctcccactgc ctgaggaagg gctgcaacac   1500
aactgccttg atatcctggc cgaagcccac ggaacccgac ccgacctaac ggaccagccg   1560
ctcccagacg ccgaccacac ctggtacacg gatggaagca gtctcttaca agagggacag   1620
cgtaaggcgg gagctgcggt gaccaccgag accgaggtaa tctgggctaa agcctgcca    1680
```

-continued

```
gccgggacat ccgctcagcg ggctgaactg atagcactca cccaggccct aaagatggca    1740
gaaggtaaga agctaaatgt ttatactgat agccgttatg cttttgctac tgcccatatc    1800
catggagaaa tatacagaag gcgtgggttg ctcacatcag aaggcaaaga gatcaaaaat    1860
aaagacgaga tcttggccct actaaaagcc ctctttctgc ccaaaagact tagcataatc    1920
cattgtccag gacatcaaaa gggacacagc gccgaggcta gaggcaaccg gatggctgac    1980
caagcggccc gaaaggcagc catcacagag actccagaca cctctaccct cctctaa      2037
```